US009820982B2

(12) United States Patent
Kao et al.

(10) Patent No.: US 9,820,982 B2
(45) Date of Patent: *Nov. 21, 2017

(54) OXYMORPHONE CONTROLLED RELEASE FORMULATIONS

(75) Inventors: Huai-Hung Kao, Syosset, NY (US); Anand R. Baichwal, Wappingers Falls, NY (US); Troy McCall, Germantown, TN (US); David Lee, Wilmington, DE (US)

(73) Assignee: ENDO PHARMACEUTICALS INC., Malvern, PA (US)

( * ) Notice: Subject to any disclaimer, the term of this patent is extended or adjusted under 35 U.S.C. 154(b) by 369 days.

This patent is subject to a terminal disclaimer.

(21) Appl. No.: 10/190,192

(22) Filed: Jul. 3, 2002

(65) Prior Publication Data

US 2003/0157167 A1    Aug. 21, 2003

Related U.S. Application Data

(60) Provisional application No. 60/329,445, filed on Oct. 15, 2001, provisional application No. 60/329,432, (Continued)

(51) Int. Cl.
| | |
|---|---|
| *A61K 31/485* | (2006.01) |
| *A61K 9/20* | (2006.01) |
| *A61K 9/24* | (2006.01) |
| *A61K 47/02* | (2006.01) |
| *A61K 47/10* | (2017.01) |

(Continued)

(52) U.S. Cl.
CPC .......... *A61K 31/485* (2013.01); *A61K 9/0053* (2013.01); *A61K 9/205* (2013.01); *A61K 9/2009* (2013.01); *A61K 9/209* (2013.01); *A61K 9/2018* (2013.01); *A61K 9/2054* (2013.01); *A61K 47/02* (2013.01); *A61K 47/10* (2013.01);

(Continued)

(58) Field of Classification Search
CPC ........ A61K 47/02; A61K 47/10; A61K 47/26; A61K 47/36; A61K 47/38; A61K 9/0053; A61K 9/20; A61K 9/205; A61K 9/209; A61K 9/2018; A61K 9/2054; A61K 9/2009; A61K 31/485
USPC .................. 424/464, 451, 489, 490; 514/536
See application file for complete search history.

(56) References Cited

U.S. PATENT DOCUMENTS

| | | | |
|---|---|---|---|
| 2,806,033 | A | 9/1957 | Lewenstein et al. |
| 3,393,197 | A | 7/1968 | Pachter et al. |

(Continued)

FOREIGN PATENT DOCUMENTS

| | | | |
|---|---|---|---|
| CA | 2452872 A1 | 1/2003 | |
| CA | 2452874 A1 | 1/2003 | |

(Continued)

OTHER PUBLICATIONS

Ansel et al. Pharmaceutical dosage forms and drug delviery systems. 1999, 7th edition, p. 121-122.*

(Continued)

*Primary Examiner* — Lakshmi Channavajjala
(74) *Attorney, Agent, or Firm* — Mayer Brown LLP

(57) ABSTRACT

The invention pertains to a method of relieving pain by administering a controlled release pharmaceutical tablet containing oxymorphone which produces a mean minimum blood plasma level 12 to 24 hours after dosing, as well as the tablet producing the sustained pain relief.

71 Claims, 10 Drawing Sheets

PK Profile for 6-OH-Oxymorphone with PID Scores

* Pain Intensity Difference    ● 6-OH-Oxymorphone Plasma Concentrations

Related U.S. Application Data filed on Oct. 15, 2001, provisional application No. 60/303,357, filed on Jul. 6, 2001, provisional application No. 60/329,444, filed on Oct. 15, 2001.

(51) Int. Cl.
*A61K 47/26* (2006.01)
*A61K 47/36* (2006.01)
*A61K 47/38* (2006.01)
*A61K 9/00* (2006.01)

(52) U.S. Cl.
CPC .............. *A61K 47/26* (2013.01); *A61K 47/36* (2013.01); *A61K 47/38* (2013.01)

(56) References Cited

U.S. PATENT DOCUMENTS

| | | | |
|---|---|---|---|
| 3,845,770 A | 11/1974 | Theeuwes et al. | |
| 4,303,691 A | 12/1981 | Sand et al. | |
| 4,366,159 A | 12/1982 | Magruder | |
| 4,569,937 A * | 2/1986 | Baker et al. | 514/282 |
| 4,711,782 A | 12/1987 | Okada et al. | |
| 4,795,642 A | 1/1989 | Cohen et al. | |
| 4,859,461 A | 8/1989 | Chow et al. | |
| 4,861,598 A | 8/1989 | Oshlack | |
| 4,994,276 A | 2/1991 | Baichwal et al. | |
| 5,047,248 A * | 9/1991 | Calanchi et al. | 424/485 |
| 5,128,143 A * | 7/1992 | Baichwal et al. | 424/464 |
| 5,266,331 A * | 11/1993 | Oshlack et al. | 424/468 |
| 5,378,462 A | 1/1995 | Boedecker et al. | |
| 5,399,359 A | 3/1995 | Baichwal et al. | |
| 5,399,362 A | 3/1995 | Baichwal et al. | |
| 5,415,871 A * | 5/1995 | Pankhania et al. | 424/468 |
| 5,431,922 A | 7/1995 | Nicklasson | |
| 5,455,046 A | 10/1995 | Baichwal | |
| 5,470,584 A | 11/1995 | Hendrickson et al. | |
| 5,478,577 A * | 12/1995 | Sackler et al. | 424/489 |
| 5,543,434 A | 8/1996 | Weg | |
| 5,554,387 A | 9/1996 | Baichwal | |
| 5,556,837 A | 9/1996 | Nestler et al. | |
| 5,662,933 A | 9/1997 | Baichwal et al. | |
| 5,672,360 A | 9/1997 | Sackler et al. | |
| 5,686,107 A | 11/1997 | Ratnaraj et al. | |
| 5,709,882 A | 1/1998 | Lindstedt et al. | |
| 5,914,131 A | 6/1999 | Merrill et al. | |
| 5,958,452 A | 9/1999 | Oshlack et al. | |
| 5,958,456 A | 9/1999 | Baichwal et al. | |
| 5,958,458 A | 9/1999 | Noring et al. | |
| 5,965,161 A | 10/1999 | Oshlack et al. | |
| 5,968,551 A | 10/1999 | Oshlack et al. | |
| 6,039,980 A | 3/2000 | Baichwal et al. | |
| 6,093,420 A * | 7/2000 | Baichwal | 424/468 |
| 6,143,322 A | 11/2000 | Sackler et al. | |
| 6,143,325 A | 11/2000 | Dennis et al. | |
| 6,143,353 A | 11/2000 | Oshlack et al. | |
| 6,221,393 B1 | 4/2001 | Collaueri et al. | |
| 6,228,398 B1 | 5/2001 | Devane et al. | |
| 6,242,001 B1 | 6/2001 | Bruce et al. | |
| 6,245,351 B1 | 6/2001 | Nara et al. | |
| 6,245,356 B1 | 6/2001 | Baichwal | |
| 6,261,599 B1 | 7/2001 | Oshlack et al. | |
| 6,294,195 B1 | 9/2001 | Oshlack et al. | |
| 6,309,668 B1 | 10/2001 | Bastin et al. | |
| 7,276,250 B2 | 10/2007 | Baichwal et al. | |
| 8,309,122 B2 | 11/2012 | Kao et al. | |
| 8,329,216 B2 | 12/2012 | Kao et al. | |
| 2001/0008639 A1 | 7/2001 | Oshlack et al. | |
| 2001/0033865 A1 | 10/2001 | Oshlack et al. | |
| 2001/0036476 A1 | 11/2001 | Oshlack et al. | |
| 2002/0044966 A1 | 4/2002 | Bartholomaeus et al. | |
| 2002/0165248 A1 | 11/2002 | Wimmer et al. | |
| 2003/0091635 A1 | 5/2003 | Baichwal et al. | |
| 2003/0118641 A1 | 6/2003 | Maloney et al. | |
| 2003/0129234 A1 | 7/2003 | Baichwal et al. | |
| 2003/0130297 A1 | 7/2003 | Kao et al. | |
| 2003/0157167 A1 | 8/2003 | Kao et al. | |
| 2007/0098792 A1 | 5/2007 | Kao et al. | |
| 2007/0098793 A1 | 5/2007 | Kao et al. | |
| 2007/0098794 A1 | 5/2007 | Kao et al. | |
| 2007/0140975 A1 | 6/2007 | Baichwal et al. | |
| 2008/0085303 A1 | 4/2008 | Baichwal et al. | |
| 2008/0085304 A1 | 4/2008 | Baichwal et al. | |
| 2008/0085305 A1 | 4/2008 | Baichwal et al. | |
| 2009/0124638 A1 | 5/2009 | Shokat et al. | |

FOREIGN PATENT DOCUMENTS

| | | |
|---|---|---|
| CA | 2251816 C | 7/2004 |
| CA | 2620224 A1 | 3/2007 |
| CA | 2321369 C | 7/2007 |
| CA | 2461157 C | 8/2007 |
| CA | 2305183 C | 9/2008 |
| CA | 2452871 C | 10/2011 |
| CN | 1551770 A | 12/2004 |
| EP | 360562 A2 * | 3/1990 |
| EP | 360562 B2 | 3/1990 |
| EP | 0864325 A2 | 9/1998 |
| ES | 2267301 T3 | 3/2007 |
| GB | 1517480 A | 7/1978 |
| GB | 2176999 B | 7/1989 |
| IN | 209411 A1 | 8/2007 |
| IN | 238365 A1 | 2/2010 |
| JP | 52-10415 A | 1/1997 |
| JP | 09136845 A | 5/1997 |
| JP | 09295933 A | 11/1997 |
| JP | 2003518489 A | 6/2003 |
| JP | 2010505948 A | 2/2010 |
| WO | WO 80/00841 | 5/1980 |
| WO | 90/03165 A1 | 4/1990 |
| WO | 93/01803 A1 | 2/1993 |
| WO | 93/10765 A1 | 6/1993 |
| WO | 93/17673 A1 | 9/1993 |
| WO | 95/28916 A1 | 11/1995 |
| WO | 97/39050 A1 | 10/1997 |
| WO | 98/00143 A1 | 1/1998 |
| WO | 99/01111 A1 | 1/1999 |
| WO | 99/17748 A1 | 4/1999 |
| WO | 99/18932 A1 | 4/1999 |
| WO | 00/07569 A1 | 2/2000 |
| WO | 00/61116 A2 | 10/2000 |
| WO | WO 01/08661 A2 | 2/2001 |
| WO | 01/22940 A1 | 4/2001 |
| WO | 01/32148 A1 | 5/2001 |
| WO | 02/28383 A1 | 4/2002 |
| WO | 03/004033 A1 | 1/2003 |
| WO | 03/013538 A1 | 2/2003 |
| WO | 2007/016563 A2 | 2/2007 |
| WO | 2007/103293 A2 | 9/2007 |
| WO | 2008/045046 A1 | 4/2008 |
| WO | 2008/045047 A1 | 4/2008 |
| WO | 2008/045060 A1 | 4/2008 |

OTHER PUBLICATIONS

Cone et al. Oxymorphone Metabolism and Urinary Excretion in Human, Rat, Guinea Pig, Rabbit and Dog. Drug metabolism and dispotition, vol. 11, No. 5, pp. 446-450.*

Chiao et al., Sustained-Release Drug Delivery Systems, Chapter 94.

Weiss, Derivatives of Morphine, I. 14-Hydroxydihydromorphinone, Nov. 20, 1995, vol. 77, pp. 5891-5892.

Dhopeshwarkar et al., "Evaluation of Xanthan Gum in the Preparation of Sustained Release Matrix Tablets", Drug Development & Industrial Pharmacy, 19(9), 1993, pp. 999-1017.

Cass, Use of Oral Analgesic for Severe Pain, Western Medicine, p. 107-108, 120 (Mar. 1961).

Numorphan Oral Advertisement, British Journal of Anaesthesia, vol. 34, No. 8 (Aug. 1962).

News of Products and Services, Products for Dispensing: Numorphan Oral, The Pharmaceutical Journal (Jul. 7, 1962).

Sargent et al., Hydroxylated Codeine Derivatives, J. Org. Chem., vol. 23 at 1247 (Sep. 1958).

(56) References Cited

OTHER PUBLICATIONS

Weiss, Derivatives of Morphine. IV. 14-Hydroxymorphine and 14-Hydroxydihydromorphine, J. Med. Chem., vol. 8 at 123 (Jan. 1965).
Final Written Decision entered on Jul. 22, 2015; *Amneal Pharmaceuticals, LLC v. Endo Pharmaceuticals Inc.*; Case No. IPR2014-00360 (34 pages).
Findings of Fact and Conclusions of Law dated Aug. 14, 2015 (Redacted); *Endo Pharmaceuticals Inc. et al. v. Amneal Pharmaceuticals, LLC et al.*; Case No. 1:12-cv-8115-TPG-GWG (159 pages).
Judgment dated Aug. 24, 2015; *Endo Pharmaceuticals Inc. et al. v. Amneal Pharmaceuticals, LLC et al.*; Case No. 1:12-cv-8115-TPG-GWG (15 pages).
U.S. District Court Civil Docket retrieved on Oct. 2, 2015; *Endo Pharmaceuticals Inc. et al. v. Amneal Pharmaceuticals, LLC et al.*; U.S. District—New York Southern; Case No. 1:12-cv-8115 (36 pages).
Supplementary European Search Report issued in EP 02773571, dated May 7, 2010.
International Search Report issued in PCT/US2006/039767, dated Sep. 4, 2007.
International Search Report issued in PCT/US2006/039923, dated Jun. 13, 2007.
Yihong Qiu & Guohua Zhang; "Research & Development Aspects of Oral Controlled-Release Dosage Forms;" in Handbook of Pharmaceutical Controlled Release Technology; Donald Wise ed.; 2000; pp. 465, 474, and 476-477.
Sathyan et al.; "Pharmacokinetic Profile of a 24-hour Controlled-Release Oros® Formulation of Hydromorphone in the Presence and Absence of Food;" BMC Clinical Pharmacology; 7:2; 2007; 8 pages.
Agrawal et al; "Wet Granulation Fine Particle Ethylcellulose Tablets: Effect of Production Variables and Mathematical Modeling of Drug Release;" AAPS PharmSci 2003; 5(2); Article 13; 2003; 13 pages.
Anonymous; "FDA Approval for Extended- and Immediate-Release Oxymorphone Hydrochloride: Oxymorphone Hydrochloride (310299)," Internet Article, Jun. 26, 2006, XP 002440904, 2 pages.
Garcia-Ochoa et al.; "Xanthan Gum: Production, Recovery and Properties;" Biotechnology Advances; vol. 18; pp. 549-579, 2000.
Johnson et al.; "Effect of Concomitant Ingestion of Alcohol on the In Vivo Pharmacokinetics of Kadian (Morphine Sulfate Extended-Release) Capsules;" The American Pain Society; available at PMID: 18201934; Jan. 15, 2008; 8 pages.
Meyer et al.; "Mitigating the Risks of Ethanol Induced Dose Dumping From Oral Sustained/Controlled Release Dosage Forms;" FDA's ACPS Meeting; Oct. 2005; 4 pages (XP002409099).
Gupta & Robinson, "Oral Controlled-Release Delivery;" in Handbook of Pharmaceutical Controlled Release Technology; Donald Wise ed.; 2000; pp. 255-258 and 273-274.
Collett & Moreton; "Modified-Release Peroral Dosage Forms" in Pharmaceutics: The Science of Dosage Form Design; Michael E. Aulton ed., 2nd edition, 2002; pp. 289 and 294-295.
Leszek Krówczynski; "Extend-Release Dosage Forms;" 1987; pp. 28 and 206.
Investigation of Bioequivalence and Bioavailability; 3CC15a; Date of Entry: 1992; 14 pages.
Guidelines on the Investigation of Bioequivalence; Committee for Medicinal Products for Human Use (CHMP); European Medicines Agency; 2010; 27 pages.
Flores, J.; Farmacologia Humana; 3rd edition; . Masson, S. A.; 1997; p. 56.
Sellers et al.; Oral Intact Extended-Release Oxymorphone is Associated With less Cognitive and Psychomotor Impairment Than Equianalgesic Doses of Oral Intact Controlled-Release Oxycodone in Healthy Nondependent Recreational Opioid User; APS 2010—Likability-Cognition Submitted Abstract; abstract 182; 1 page.
Sellers et al.; Oral Intact Extended-Release Oxymorphone is Associated With less liking and Lower Positive Subjective Effects than Equianalgesic Doses of Oral Intact Controlled-Release Oxycodone in Healthy Nondependent Recreational Opioid Users, APS 2010—Likability-Cognition Submitted Abstract; abstract 183; 1 page.
U.S. Pharmacopeia: National Formulary; USP23 NF18; 1995; pp. 1791-1799.
Thirlwell et al.; "Pharmacokinetics and Clinical Efficacy of Oral Morphine Solution and Controlled-Release Morphine Tablets in Cancer Patients;" Cancer; 63: 2275-2283; 1989.
Goughnour et al; "Analgesic Response to Single and Multiple Doses of Controlled-Release Morphine Tablets and Morphine Oral Solution in Cancer Patients;" Cancer; 63: 2294-2297; 1989.
Ferrell et al.; "Effects of Controlled-Release Morphine on Quality of Life for Cancer Pain;" Oncology Nursing Forum; 16 (4); 521-526; 1989.
Harden et al.; "Opioids, Substance Abuse & Addictions Section: Negligible Analgesic Tolerance Seen with Extended Release Oxymorphone: A Post Hoc Analysis of Open-Label Longitudinal Data;" Pain Medicine; vol. 11; issue 8;1198-1208; 2010.
Berner et al.; "A Comparison of Daily Average Consumption of Oxycodone Controlled Release (OxyContin CR) and Oxymorphone Extended Release (Opana ER) in Patients With Low Back Pain;" P&T; vol. 36; No. 3; pp. 139-144; 2011.
Schoedel et al.; "Positive and Negative Subjective Effects of Extended-Release Oxymorphone Versus Controlled-Release Oxycodone in Recreational Opioid Users;" Journal of Opioid Management; 7:3; pp. 179-192; 2011.
Schoedel et al.; "Reduced Cognitive and Psychomotor Impairment With Extended-Release Oxymorphone Versus Controlled-Release Oxycodone;" Pain Physician; 13; pp. 561-573; 2010.
Rubino et al.; "A Comparison of Daily Average Consumption (DACON) of Oxycodone and Oxymorphone Long-Acting Oral Tablets;" Journal of Managed Care Pharmacy; vol. 17; No. 5; pp. 367-376; 2011.
David R. P. Guay; "Oral Hydromorphone Extended-Release;" The Consultant Pharmacist; vol. 25(12); pp. 816-828; 2010.
Slatkin et al.; "Long-Term Tolerability and Effectiveness of Oxymorphone Extended Release in Patients with Cancer;" Journal of Opioid Management; vol. 6; No. 3; pp. 181-191; 2010.
Rauck et al.; "Titration With Oxymorphone Extended Release to Achieve Effective Long-Term Pain Relief and Improve Tolerability in Opioid-Naïve Patients with Moderate to Severe Pain;" Pain Medicine; vol. 9; No. 7; pp. 777-785; 2008.
Gimbel, Joseph; "Oxymorphone: A Mature Molecule With New Life;" Drugs of Today; 44 (10); pp. 767-782; 2008.
Mayyas, et al.; "A Systematic Review of Oxymorphone in the Management of Chronic Pain;" Journal of Pain and Symptom Management; vol. 39; No. 2; pp. 296-308; 2010.
Peniston et al.; "Factors Affecting Acceptability of Titrated Oxymorphone Extended Release in Chronic Low Back Pain—An Individual Patient Analysis;" Current Medical Research & Opinion; vol. 26; No. 8; pp. 1861-1871; 2010.
Kaye et al.; "Pain Management in the Elderly Population: A Review;" The Ochsner Journal; vol. 10; 179-187; 2010.
Craig, D. S.; "Oxymorphone Extended-Release Tablets (Opana ER) for the Management of Chronic Pain: A Practical Review for Pharmacists;" P&T; vol. 35; No. 6; 324-357; 2010.
Sriwongjanya et al.; "Effect of Ion Exchange Resins on the Drug Release From Matrix Tablets;" European Journal of Pharmaceutics and Biopharmaceutics; vol. 46; No. 3; pp. 321-327; 1998.
Hussain, Ajaz S.; "Preventing Alcohol Induced Dose Dumping is a Desired Product Design Feature;" Oct. 26, 2005; Retrieved from the Internet: http://www.fda.gov/ohrms/dockets/ac/05/slides/2005-4187S2_02_Hussain_files/frame.htm [slides 1-13] (XP002409100).
Roberts et al; "Influence of Ethanol on Aspirin Release From Hypromellose Matrices;" International Journal of Pharmaceutics; vol. 332; pp. 31-37; 2007.
"Alcohol-Associated Rapid Release of a Long-Acting Opioid;" CMAJ; vol. 173; No. 7; p. 756; 2005.
Declaration of Dr. Sou-Chan Chang, dated Apr. 7, 2008; filed in U.S. Appl. No. 11/680,432.
Declaration of Dr. Sou-Chan Chang, dated May 21, 2008; filed in U.S. Appl. No. 11/680,432.

(56) References Cited

OTHER PUBLICATIONS

Declaration of Dr. David C. Yeomans, dated May 6, 2008; filed in U.S. Appl. No. 11/680,432.
Declaration of William Fiske, dated May 22, 2008; filed in U.S. Appl. No. 11/680,432.
Declaration of Nancy Wysenski, dated Mar. 28, 2008; filed in U.S. Appl. No. 11/680,432.
Particle Size Conversion Table; Sigma Aldrich; Chemicals—Technical Library (2 pages). http://www.sigmaaldrich.com/chemistry/stockroom-reagents/learning-center/technical-library/particle-size-conversion.html.
International Search Report issued in PCT/US1995/03825, dated Jun. 19, 1995.
International Search Report issued in PCT/US2002/30393, dated Mar. 14, 2003.
International Search Report issued in PCT/US2006/039781, dated Sep. 3, 2007.
Decision by the United States Court of Appeals for the Federal Circuit in U.S. Appl. No. 11/680,432; dated May 13, 2011.
Decision by the Board of Patent Appeals and Interferences in U.S. Appl. No. 11/680,432; dated Aug. 13, 2012.
Petition for Inter Partes Review of U.S. Pat. No. 8,329,216 filed in IPR 2014-00360 and dated Jan. 16, 2014.
Declaration of Vivian A. Gray filed in IPR 2014-00360 and dated Jan. 16, 2014.
Declaration of Anthony Palmieri III filed in IPR 2014-00360 and dated Jan. 16, 2014.
The United States Pharmacopeia 24: The National Formulary 19, pp. 8, 1941-1943 (1999).
The Handbook of Dissolution Testing, 2nd ed., Revised, Hanson, W.A., ed., pp. v-xii, 1-13, 26-53, 69-91, 111-123 (1991).
Penwest Pharmaceuticals Co.'s Form S-1 Registration Statement Under the Securities Act of 1953 (1997).
Gordon et al., "Opioid Equianalgesic Calculations," Journal of Palliative Medicine 2(2):209-218 (1999).
Poulain et al., "Relative Bioavailability of Controlled Release Morphine Tablets (MST Continus) in Cancer Patients," J. Anaesth. 61:569-574 (1988). Br.
Physicians' Desk Reference, 54th ed., Numorphan®, pp. 1036 and 1037 (2000).
"TIMERx Oral Controlled-Release Drug Delivery System," by McCall et al., in Modified-Release Drug Delivery Technology, Chapter 2, Rathbone et al., eds., pp. 11-19 (2007).
Handbook of Pharmaceutical Excipients, 3rd ed., Kibbe, A., ed., pp. 252-255 and 599-601 (2000).
Laboratory Notebook, Project PD161-02, pp. 1-3, dated Nov. 13-14, 2013.
Laboratory Notebook, Notebook No. PD162, Amneal Pharmaceuticals, assigned to Dilip Makwana, pp. 1-39, dated Nov. 14-21, 2013.
Product Lot #PD161-01, R&D Analytical Laboratory, Amneal Pharmaceutical of NY, LLC, Calculation Sheet for Dissolution of Tablets/Capsules by HPLC/UPLC, Oxymorphone HCL ER Tablet.
Product Lot #PD161-02, R&D Analytical Laboratory, Amneal Pharmaceutical of NY, LLC, Calculation Sheet for Dissolution of Tablets/Capsules by HPLC/UPLC, Oxymorphone HCL ER Tablet.
Re: *Endo Pharms., Inc.* v. *Amneal Pharms., LLC*, Case No. 1:12-cv-8115 (S.D.N.Y.) Formulation and Testing Protocol of Controlled-Release Oxymorphone Tablets, dated Nov. 11, 2013, 3 pages.
Notice of Filing Date Accorded to Petition and Time for Filing Patent Owner Preliminary Response in IPR 2014-00360, dated Jan. 28, 2014.
Patent Owner's Notice and Designation filed in IPR 2014-00360, dated Feb. 18, 2014.
Patent Owner's Preliminary Response filed in IPR 2014-00360, dated Apr. 25, 2014.
Complaint filed Nov. 7, 2012 (CA No. 1:12-cv-08115) (S.D.N.Y.).
Amended Complaint filed Nov. 14, 2012 (CA No. 1:12-cv-08115) (S.D.N.Y.).
Affidavit of Service establishing service of Summons and Amended Complaint on Nov. 20, 2012 (CA No. 1:12-cv-08115) (S.D.N.Y.).
Unopposed Motion for Leave to file Second Amended Complaint filed Jan. 9, 2013 with Second Amended Complaint attached as an exhibit hereto (CA No. 1:12-cv-08115) (S.D.N.Y.).
Notice of Electronic Filing of Unopposed Motion for Leave to File Second Amended Complaint transmitted on Jan. 9, 2013 (CA No. 1:12-cv-08115) (S.D.N.Y.).
Order granting Unopposed Motion for Leave to file Second Amended Complaint on Jan. 14, 2013 (CA No. 1:12-cv-08115) (S.D.N.Y.).
Second Amended Complaint as filed on Jan. 17, 2013 (CA No. 1:12-cv-08115) (S.D.N.Y.).
Court Docket as of Apr. 24, 2014 (CA No. 1:12-cv-08115) (S.D.N.Y.).
Southern District of New York Electronic Case Filing Rules and Instructions.
Order regarding Conducting a Proceeding in IPR 2014-00360, dated May 8, 2014.
Petitioner's Reply Brief filed in IPR 2014-00360, dated May 15, 2014.
Transcript of Patent Trial and Appeal Board Teleconference before Judges Scheiner, Prats and Bonilla in Cases IPR2014-00360 and 2014-00361, Wednesday, May 7, 2014.
Letter from Petitioner's litigation counsel to United States Magistrate Judge Gorenstein dated Jan. 10, 2013.
Petition for Inter Partes Review of U.S. Pat. No. 8,309,122 filed in IPR 2014-00361 and dated Jan. 16, 2014.
Declaration of Vivian A. Gray filed in IPR 2014-00361 and dated Jan. 16, 2014.
Declaration of Anthony Palmieri III filed in IPR 2014-00361 and dated Jan. 16, 2014.
Notice of Filing Date Accorded to Petition and Time for Filing Patent Owner Preliminary Response filed in IPR 2014-00361, dated Jan. 28, 2014.
Patent Owner's Notice and Designation filed in IPR 2014-00361, dated Feb. 18, 2014.
Patent Owner's Preliminary Response filed in IPR 2014-00361, dated Apr. 25, 2014.
Order regarding Conducting a Proceeding in IPR 2014-00361, dated May 8, 2014.
Petitioner's Reply Brief filed in IPR 2014-00361, dated May 15, 2014.
Email from Jonathan Loeb to Paul Ainsworth and Courtney Macdonald, dated Jan. 7, 2013.
Patent Owner's Surreply Regarding 35 U.S.C. § 315(b) filed in IPR 2014-00360 and dated May 22, 2014.
Patent Owner's Surreply Regarding 35 U.S.C. § 315(b) filed in IPR 2014-00361 and dated May 22, 2014.
Laboratory Notebook, Notebook No. PD162, Amneal Pharmaceuticals, assigned to Dilip Makwana, pp. 1-39, dated Nov. 14-21, 2013, from IPR2014-00361.
"Guidance for Industry Bioavailability and Bioequivalence Studies for Orally Administered Drug Products — General Considerations;" U.S. Department of Health and Human Services; Food and Drug Administration Center for Drug Evaluation and Research (CDER); Mar. 2003; Revision 1; 26 pages.
Wang et al.; "Biorelevant Dissolution: Methodology and Application in Drug Development:" Dissolution Technologies; pp. 6-12; 2009.
Fotaki et al.; "Biorelevant Dissolution Methods and Their Applications in In Vitro-In Vivo Correlations for Oral Formulations;" The Open Drug Delivery Journal; 4; pp. 2-13; 2010.
Murtaza et al,; "Development of In Vitro-In Vivo Correlation for Pharmacokinetic Simulation;" African Journal of Pharmacy and Pharmacology; vol. 6(4); pp. 257-263; 2012.
"Guidance for Industry Extended Release Oral Dosage Forms: Development, Evaluation, and Application of In Vitro/In Vivo Correlations;" U.S. Department of Health and Human Services; Food and Drug Administration Center for Drug Evaluation and Research (CDER); 1997; BP 2; 27 pages.
Tiwari et al.; "In vitro-In vivo correlation and biopharmaceutical classification system;" Chronicles of Young Scientists; vol. 2; Issue

(56) References Cited

OTHER PUBLICATIONS

3; 2011; pp. 126-133. [Downloaded from http://www.cysonline.org on Apr. 1, 2014, IP: 143.58.161.6].

Cardot et al.; "In Vitro-In Vivo Correlation: Importance of Dissolution in IVIVC;" Dissolution Technologies; 2007; pp. 15-19.

Michael Aulton; "Dissolution & Solubility;" in Pharmaceutics: The Science of Dosage Form Design; 15, 19-25 (Michael E. Aulton ed., 2d ed. 2002).

Peter York; "The Design of Dosage Forms;" in Pharmaceutics: The Science of Dosage Form Design 1-10 (Michael E. Aulton ed., 2d ed. 2002).

Petition for Inter Partes Review of U.S. Pat. No. 8,329,216 dated Jan. 16, 2014; Case No. IPR2014-00360 (62 pages).

Decision of Institution of Inter Partes Review dated Jul. 25, 2014; Case No. IPR2014-00360 (23 pages).

Redacted Version of the Patent Owner's Response dated Oct. 27, 2014; Case No. IPR2014-00360 (69 pages).

Redacted Version of the Petitioner's Reply to Patent Owner's Response dated Jan. 26, 2015; Case No. IPR2014-00360 (18 pages).

Supplemental Patent Owner's Response dated Mar. 4, 2015; Case Nos. IPR2014-00360 and IPR2014-01365 (12 pages).

Petitioner's Reply to Patent Owner's Supplemental Response dated Apr. 1, 2015; Case Nos. IPR2014-00360 and IPR2014-01365 (8 pages).

Final Written Decision dated Jul. 22, 2015; Case Nos. IPR2014-00360 and IPR2014-01365 (34 pages).

Petition for Inter Partes Review of U.S. Pat. No. 8,329,216 dated Aug. 22, 2014; Case No. IPR2014-01365 (58 pages).

Decision Granting Petitioner's Motion for Joinder In-Part, and Instituting Inter Partes Review dated Feb. 4, 2015; Case No. IPR2014-01365 (21 pages).

Petition for Inter Partes Review of U.S. Pat. No. 8,309,122 dated Jan. 16, 2014; Case No. IPR2014-000361 (60 pages).

Decision Denying Institution of Inter Partes Review dated Jul. 25, 2014; Case No. IPR2014-00361 (8 pages).

Appellant Amneal Pharmaceuticals, LLC's Opening Brief dated Jan. 19, 2016; United States Court of Appeals for the Federal Circuit; Case No. 16-1217 (150 pages).

Brief of Appellee Endo Pharmaceuticals Inc. dated Apr. 29, 2016; United States Court of Appeals for the Federal Circuit; Case No. 16-1217 (89 pages).

Appellant Amneal Pharmaceuticals, LLC's Reply Brief dated Jun. 13, 2016; United States Court of Appeals for the Federal Circuit; Case No. 16-1217 (47 pages).

Order dated Aug. 14, 2015; United States District Court, Southern District of New York; Case No. 1:13-cv-04343 (4 pages).

Judgment of the U.S. Court of Appeals for the Federal Circuit dated Nov. 8, 2016; United States Court of Appeal for the Federal Circuit; Case No. 16-1217 (2 pages).

\* cited by examiner

OXYMORPHONE CONTROLLED RELEASE FORMULATIONS

This application relates to provisional patent application Ser. No. 60/329,445 filed Oct. 15, 2001, No. 60/329,432 filed Oct. 15, 2001, No. 60/303,357 filed Jul. 6, 2001, and 60/329,444 filed Oct. 15, 2001.

BACKGROUND OF THE INVENTION

Pain is the most frequently reported symptom and it is a common clinical problem which confronts the clinician. Many millions of people in the USA suffer from severe pain that, according to numerous recent reports, is chronically undertreated or inappropriately managed. The clinical usefulness of the analgesic properties of opioids has been recognized for centuries, and morphine and its derivatives have been widely employed for analgesia for decades in a variety of clinical pain states.

Oxymorphone HCl (14-hydroxydihydromorphinone hydrochloride) is a semi-synthetic phenanthrene-derivative opioid agonist, widely used in the treatment of acute and chronic pain, with analgesic efficacy comparable to other opioid analgesics. Oxymorphone is currently marketed as an injection (1 mg/ml in 1 ml ampules; 1.5 mg/ml in 1 ml ampules; 1.5 mg/ml in 10 ml multiple dose vials) for intramuscular, subcutaneous, and intravenous administration, and as 5 mg rectal suppositories. At one time, 2 mg, 5 mg and 10 mg oral immediate release (IR) tablet formulations of oxymorphone HCl were marketed. Oxymorphone HCl is metabolized principally in the liver and undergoes conjugation with glucuronic acid and reduction to 6 α- and β-hydroxy epimers.

An important goal of analgesic therapy is to achieve continuous relief of chronic pain. Regular administration of an analgesic is generally required to ensure that the next dose is given before the effects of the previous dose have worn off. Compliance with opioids increases as the required dosing frequency decreases. Non-compliance results in suboptimal pain control and poor quality of life outcomes. (Ferrell B et al. Effects of controlled-release morphine on quality of life for cancer pain. *Oncol Nur Forum* 1989; 4:521-26). Scheduled, rather than "as needed" administration of opioids is currently recommended in guidelines for their use in chronic non-malignant pain. Unfortunately, evidence from prior clinical trials and clinical experience suggests that the short duration of action of immediate release oxymorphone would necessitate administration every 4-6 hours in order to maintain optimal levels of analgesia in chronic pain. A controlled release formulation which would allow less frequent dosing of oxymorphone would be useful in pain management.

For instance, a controlled release formulation of morphine has been demonstrated to provide patients fewer interruptions in sleep, reduced dependence on caregivers, improved compliance, enhanced quality of life outcomes, and increased control over the management of pain. In addition, the controlled release formulation of morphine was reported to provide more constant plasma concentration and clinical effects, less frequent peak to trough fluctuations, reduced dosing frequency, and possibly fewer side effects. (Thirlwell M P et al., Pharmacokinetics and clinical efficacy of oral morphine solution and controlled-release morphine tablets in cancer patients. *Cancer* 1989; 63:2275-83; Goughnour B R et al., Analgesic response to single and multiple doses of controlled-release morphine tablets and morphine oral solution in cancer patients. *Cancer* 1989; 63:2294-97; Ferrell B. et al., Effects of controlled-release morphine on quality of life for cancer pain. *Oncol. Nur. Forum* 1989; 4:521-26.

There are two factors associated with the metabolism of some drugs that may present problems for their use in controlled release systems. One is the ability of the drug to induce or inhibit enzyme synthesis, which may result in a fluctuating drug blood plasma level with chronic dosing. The other is a fluctuating drug blood level due to intestinal (or other tissue) metabolism or through a hepatic first-pass effect.

Oxymorphone is metabolized principally in the liver, resulting in an oral bioavailability of about 10%. Evidence from clinical experience suggests that the short duration of action of immediate release oxymorphone necessitates a four hour dosing schedule to maintain optimal levels of analgesia. It would be useful to clinicians and patients alike to have controlled release dosage forms of oxymorphone to use to treat pain and a method of treating pain using the dosage forms.

SUMMARY OF THE INVENTION

The present invention provides methods for relieving pain by administering a controlled release pharmaceutical tablet containing oxymorphone which produces at least a predetermined minimum blood plasma level for at least 12 hours after dosing, as well as tablets that produce the sustained pain relief over this time period.

DETAILED DESCRIPTION OF THE INVENTION

Figure 1:
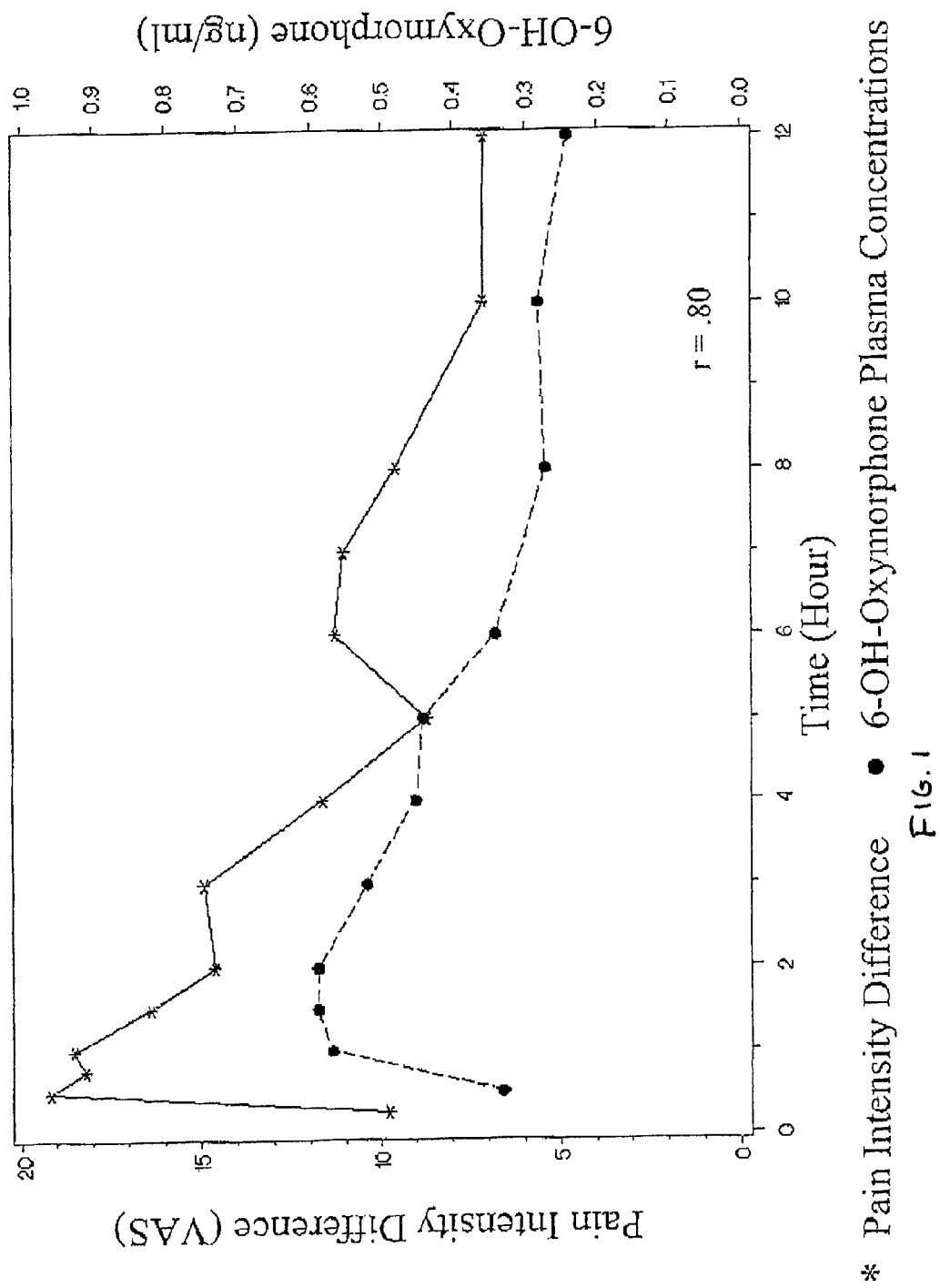
FIG. 1 is a pharmacokinetic profile for 6-hydroxy oxymorphone with PID scores.

The present invention provides methods for alleviating pain for 12 to 24 hours using a single dose of a pharmaceutical composition by producing a blood plasma level of oxymorphone and/or 6-OH oxymorphone of at least a minimum value for at least 12 hours or more. As used herein, the terms "6-OH oxymorphone" and "6-hydroxy oxymorphone" are interchangeable and refer to the analog of oxymorphone having an alcohol (hydroxy) moiety that replaces the carboxy moiety found on oxymorphone at the 6-position.

To overcome the difficulties associated with a 4-6 hourly dosing frequency of oxymorphone, this invention provides an oxymorphone controlled release oral solid dosage form, comprising a therapeutically effective amount of oxymorphone or a pharmaceutically acceptable salt of oxymorphone. It has been found that the decreased rate of release of oxymorphone from the oral controlled release formulation of this invention does not substantially decrease the bioavailability of the drug as compared to the same dose of a solution of oxymorphone administered orally. The bioavailability is sufficiently high and the release rate is such that a sufficient plasma level of oxymorphone and/or 6-OH oxymorphone is maintained to allow the controlled release dosage to be used to treat patients suffering moderate to severe pain with once or twice daily dosing. The dosing form of the present invention can also be used with thrice daily dosing.

It is critical when considering the present invention that the difference between a controlled release tablet and an immediate release formulation be fully understood. In classical terms, an immediate release formulation releases at least 80% of its active pharmaceutical ingredient within 30 minutes. With reference to the present invention, the definition of an immediate release formulation will be broadened further to include a formulation which releases more than about 80% of its active pharmaceutical ingredient within 60 minutes in a standard USP Paddle Method dissolution test at 50 rpm in 500 ml media having a pH of between 1.2 and 6.8 at 37° C. "Controlled release" formulations, as referred to herein, will then encompass any formulations which release no more than about 80% of their active pharmaceutical ingredients within 60 minutes under the same conditions.

The controlled release dosage form of this invention exhibits a dissolution rate in vitro, when measured by USP Paddle Method at 50 rpm in 500 ml media having a pH between 1.2 and 6.8 at 37° C., of about 15% to about 50% by weight oxymorphone released after 1 hour, about 45% to about 80% by weight oxymorphone released after 4 hours, and at least about 80% by weight oxymorphone released after 10 hours.

When administered orally to humans, an effective controlled release dosage form of oxymorphone should exhibit the following in vivo characteristics: (a) peak plasma level of oxymorphone occurs within about 1 to about 8 hours after administration; (b) peak plasma level of 6-OH oxymorphone occurs within about 1 to about 8 hours after administration; (c) duration of analgesic effect is through about 8 to about 24 hours after administration; (d) relative oxymorphone bioavailability is in the range of about 0.5 to about 1.5 compared to an orally-administered aqueous solution of oxymorphone; and (e) the ratio of the area under the curve of blood plasma level vs. time for 6-OH oxymorphone compared to oxymorphone is in the range of about 0.5 to about 1.5. Of course, there is variation of these parameters among subjects, depending on the size and weight of the individual subject, the subject's age, individual metabolism differences, and other factors. Indeed, the parameters may vary in an individual from day to day. Accordingly, the parameters set forth above are intended to be mean values from a sufficiently large study so as to minimize the effect of individual variation in arriving at the values. A convenient method for arriving at such values is by conducting a study in accordance with standard FDA procedures such as those employed in producing results for use in a new drug application (or abbreviated new drug application) before the FDA. Any reference to mean values herein, in conjunction with desired results, refer to results from such a study, or some comparable study. Reference to mean values reported herein for studies actually conducted are arrived at using standard statistical methods as would be employed by one skilled in the art of pharmaceutical formulation and testing for regulatory approval.

In one specific embodiment of the controlled release matrix form of the invention, the oxymorphone or salt of oxymorphone is dispersed in a controlled release delivery system that comprises a hydrophilic material which, upon exposure to gastrointestinal fluid, forms a gel matrix that releases oxymorphone at a controlled rate. The rate of release of oxymorphone from the matrix depends on the drug's partition coefficient between components of the matrix and the aqueous phase within the gastrointestinal tract. In a preferred form of this embodiment, the hydrophilic material of the controlled release delivery system comprises a mixture of a heteropolysaccharide gum and an agent capable of cross-linking the heteropolysaccharide in the presence of gastrointestinal fluid. The controlled release delivery system may also comprise a water-soluble pharmaceutical diluent mixed with the hydrophilic material. Preferably, the cross-linking agent is a homopolysaccharide gum and the inert pharmaceutical diluent is a monosaccharide, a disaccharide, or a polyhydric alcohol, or a mixture thereof.

In a specific preferred embodiment, the appropriate blood plasma levels of oxymorphone and 6-hydroxy oxymorphone are achieved using oxymorphone in the form of oxymorphone hydrochloride, wherein the weight ratio of heteropolysaccharide to homopolysaccharide is in the range of about 1:3 to about 3:1, the weight ratio of heteropolysaccharide to diluent is in the range of about 1:8 to about 8:1, and the weight ratio of heteropolysaccharide to oxymorphone hydrochloride is in the range of about 10:1 to about 1:10. A preferred heteropolysaccharide is xanthan gum and a preferred homopolysaccharide is locust bean gum. The dosage form also comprises a cationic cross-linking agent and a hydrophobic polymer. In the preferred embodiment, the dosage form is a tablet containing about 5 mg to about 80 mg of oxymorphone hydrochloride. In a most preferred embodiment, the tablet contains about 20 mg oxymorphone hydrochloride.

The invention includes a method which comprises achieving appropriate blood plasma levels of drug while providing extended pain relief by administering one to three times per day to a patient suffering moderate to severe, acute or chronic pain, an oxymorphone controlled release oral solid dosage form of the invention in an amount sufficient to alleviate the pain for a period of about 8 hours to about 24 hours. This type and intensity of pain is often associated with cancer, autoimmune diseases, infections, surgical and accidental traumas and osteoarthritis.

The invention also includes a method of making an oxymorphone controlled release oral solid dosage form of the invention which comprises mixing particles of oxymorphone or a pharmaceutically acceptable salt of oxymorphone with granules comprising the controlled release delivery system, preferably followed by directly compressing the mixture to form tablets.

Pharmaceutically acceptable salts of oxymorphone which can be used in this invention include salts with the inorganic and organic acids which are commonly used to produce nontoxic salts of medicinal agents. Illustrative examples would be those salts formed by mixing oxymorphone with hydrochloric, sulfuric, nitric, phosphoric, phosphorous, hydrobromic, maleric, malic, ascorbic, citric or tartaric, pamoic, lauric, stearic, palmitic, oleic, myristic, lauryl sulfuric, naphthylenesulfonic, linoleic or linolenic acid, and the like. The hydrochloride salt is preferred.

It has now been found that 6-OH oxymorphone, which is one of the metabolites of oxymorphone may play a role in alleviating pain. When oxymorphone is ingested, part of the dosage gets into the bloodstream to provide pain relief, while another part is metabolized to 6-OH oxymorphone. This metabolite then enters the bloodstream to provide further pain relief. Thus it is believed that both the oxymorphone and 6-hydroxyoxymorphone levels are important to pain relief.

Figure 2:
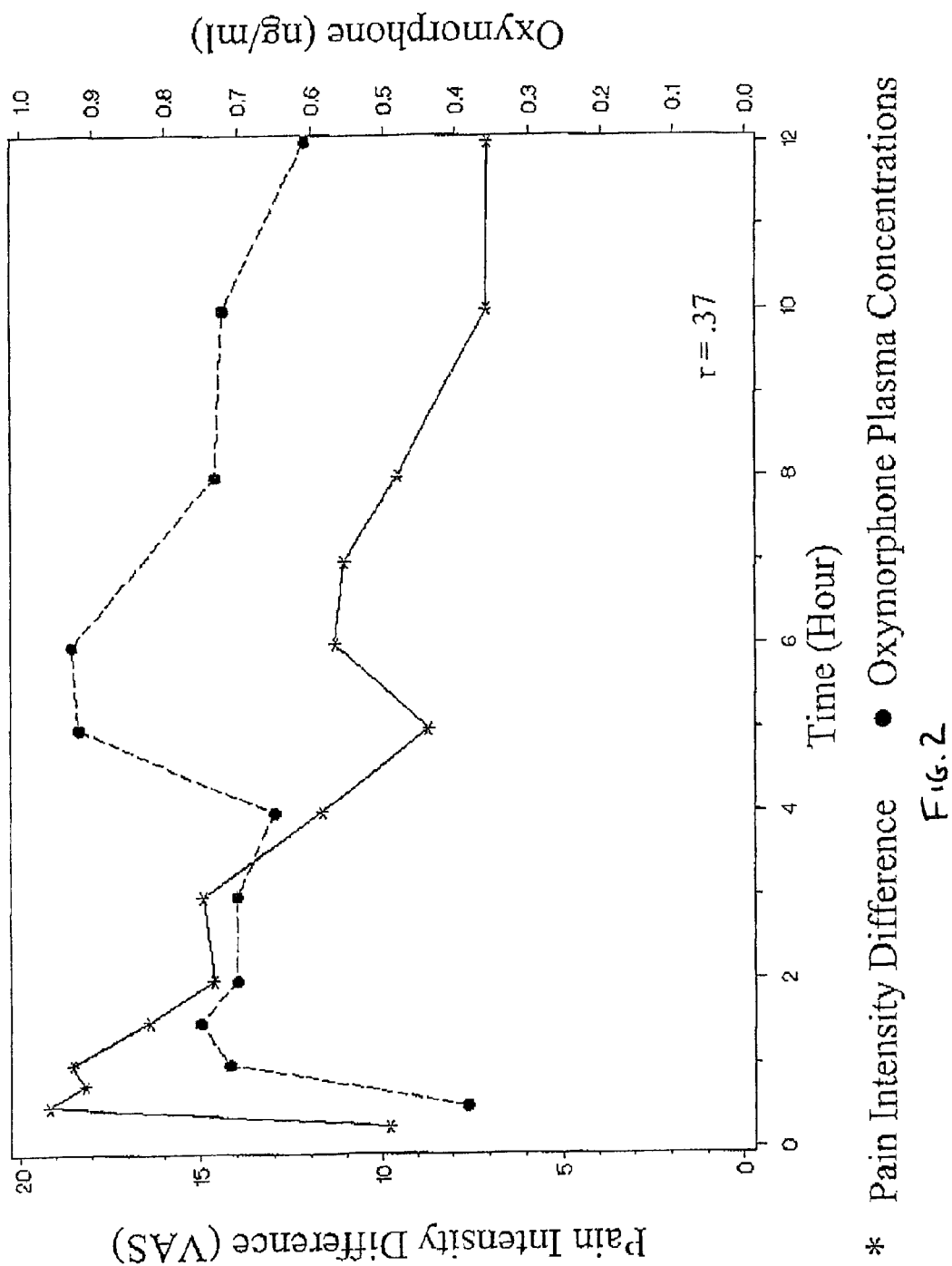
FIG. 2 is a pharmacokinetic profile for oxymorphone with PID scores.
Figure 3:
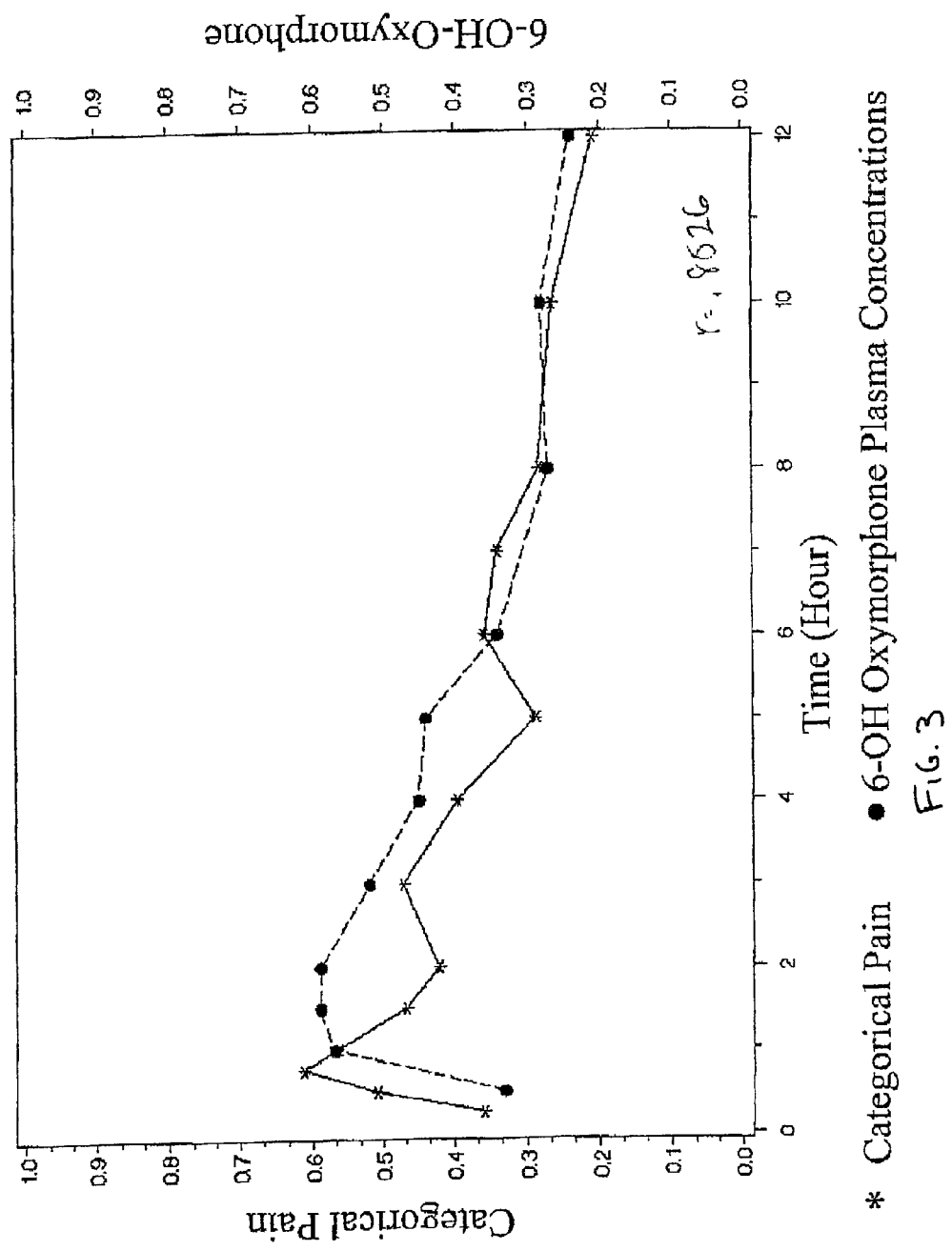
FIG. 3 is a pharmacokinetic profile for 6-hydroxy oxymorphone with categorical pain scores.
Figure 4:
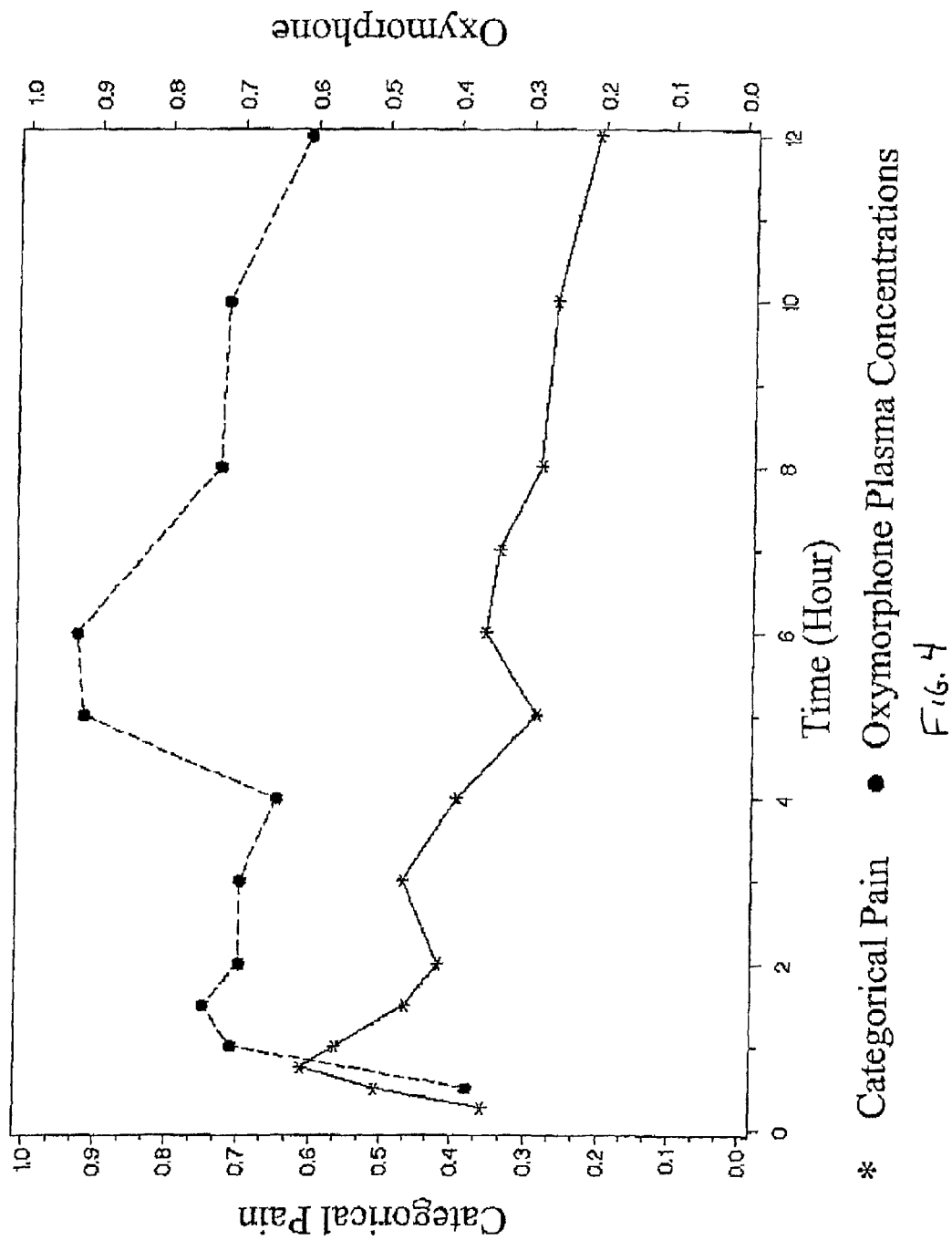
FIG. 4 is a pharmacokinetic profile for oxymorphone with categorical pain scores.

The effectiveness of oxymorphone and 6-hydroxyoxymorphone at relieving pain and the pharmacokinetics of a single dose of oxymorphone were studied. The blood plasma levels of both oxymorphone and 6-hydroxyoxymorphone were measured in patients after a single dose of oxymorphone was administered. Similarly, the pain levels in patients were measured after a single administration of oxymorphone to determine the effective duration of pain relief from a single dose. FIGS. 1-2 show the results of these tests, comparing pain levels to oxymorphone and 6-hydroxy oxymorphone levels.

For these tests, pain was measured using a Visual Analog Scale (VAS) or a Categorical Scale. The VAS scales consisted of a horizontal line, 100 mm in length. The left-hand end of the scale (0 mm) was marked with the descriptor "No Pain" and the right-hand end of the scale (100 mm) was marked with the descriptor "Extreme Pain". Patients indicated their level of pain by making a vertical mark on the line. The VAS score was equal to the distance (in mm) from the left-hand end of the scale to the patient's mark. For the categorical scale, patients completed the following statement, "My pain at this time is" using the scale None=0, Mild=1, Moderate=2, or Severe=3.

As can be seen from these figures, there is a correlation between pain relief and both oxymorphone and 6-hydroxyoxymorphone levels. As the blood plasma levels of oxymorphone and 6-hydroxyoxymorphone increase, pain decreases (and pain intensity difference and pain relief increases). Thus, to the patient, it is the level of oxymorphone and 6-hydroxyoxymorphone in the blood plasma which is most important. Further it is these levels which dictate the efficacy of the dosage form. A dosage form which maintains a sufficiently high level of oxymorphone or 6-hydroxyoxymorphone for a longer period need not be administered frequently. Such a result is accomplished by embodiments of the present invention.

The oxymorphone controlled release oral solid dosage form of this invention can be made using any of several different techniques for producing controlled release oral solid dosage forms of opioid analgesics.

In one embodiment, a core comprising oxymorphone or oxymorphone salt is coated with a controlled release film which comprises a water insoluble material and which upon exposure to gastrointestinal fluid releases oxymorphone from the core at a controlled rate. In a second embodiment, the oxymorphone or oxymorphone salt is dispersed in a controlled release delivery system that comprises a hydrophilic material which upon exposure to gastrointestinal fluid forms a gel matrix that releases oxymorphone at a controlled rate. A third embodiment is a combination of the first two: a controlled release matrix coated with a controlled release film. In a fourth embodiment the oxymorphone is incorporated into an osmotic pump. In any of these embodiments, the dosage form can be a tablet, a plurality of granules in a capsule, or other suitable form, and can contain lubricants, colorants, diluents, and other conventional ingredients.

Osmotic Pump

An osmotic pump comprises a shell defining an interior compartment and having an outlet passing through the shell. The interior compartment contains the active pharmaceutical ingredient. Generally the active pharmaceutical ingredient is mixed with excipients or other compositions such as a polyalkylene. The shell is generally made, at least in part, from a material (such as cellulose acetate) permeable to the liquid of the environment where the pump will be used, usually stomach acid. Once ingested, the pump operates when liquid diffuses through the shell of the pump. The liquid dissolves the composition to produce a saturated situation. As more liquid diffuses into the pump, the saturated solution containing the pharmaceutical is expelled from the pump through the outlet. This produces a nearly constant release of active ingredient, in the present case, oxymorphone.

Controlled Release Coating

In this embodiment, a core comprising oxymorphone or oxymorphone salt is coated with a controlled release film which comprises a water insoluble material. The film can be applied by spraying an aqueous dispersion of the water insoluble material onto the core. Suitable water insoluble materials include alkyl celluloses, acrylic polymers, waxes (alone or in admixture with fatty alcohols), shellac and zein. The aqueous dispersions of alkyl celluloses and acrylic polymers preferably contain a plasticizer such as triethyl citrate, dibutyl phthalate, propylene glycol, and polyethylene glycol. The film coat can contain a water-soluble material such as polyvinylpyrrolidone (PVP) or hydroxypropylmethylcellulose (HPMC).

The core can be a granule made, for example, by wet granulation of mixed powders of oxymorphone or oxymorphone salt and a binding agent such as HPMC, or by coating an inert bead with oxymorphone or oxymorphone salt and a binding agent such as HPMC, or by spheronising mixed powders of oxymorphone or oxymorphone salt and a spheronising agent such as microcrystalline cellulose. The core can be a tablet made by compressing such granules or by compressing a powder comprising oxymorphone or oxymorphone salt.

The in vitro and in vivo release characteristics of this controlled release dosage form can be modified by using mixtures of different water insoluble and water soluble materials, using different plasticizers, varying the thickness of the controlled release film, including release-modifying agents in the coating, or by providing passageways through the coating.

Controlled Release Matrix

It is important in the present invention that appropriate blood plasma levels of oxymorphone and 6 hydroxy oxymorphone be achieved and maintained for sufficient time to provide pain relief to a patient for a period of 12 to 24 hours. The preferred composition for achieving and maintaining the proper blood plasma levels is a controlled-release matrix. In this embodiment, the oxymorphone or oxymorphone salt is dispersed in a controlled release delivery system that comprises a hydrophilic material (gelling agent) which upon exposure to gastrointestinal fluid forms a gel matrix that releases oxymorphone at a controlled rate. Such hydrophilic materials include gums, cellulose ethers, acrylic resins, and protein-derived materials. Suitable cellulose ethers include hydroxyalkyl celluloses and carboxyalkyl celluloses, especially hydroxyethyl cellulose (HEC), hydroxypropyl cellulose (HPC), HPMC, and carboxy methylcellulose (CMC). Suitable acrylic resins include polymers and copolymers of acrylic acid, methacrylic acid, methyl acrylate and methyl methacrylate. Suitable gums include heteropolysaccharide and homopolysaccharide gums, e.g., xanthan, tragacanth, acacia, karaya, alginates, agar, guar, hydroxypropyl guar, carrageenan, and locust bean gums.

Preferably, the controlled release tablet of the present invention is formed from (I) a hydrophilic material comprising (a) a heteropolysaccharide; or (b) a heteropolysaccharide and a cross-linking agent capable of cross-linking said heteropolysaccharide; or (c) a mixture of (a), (b) and a polysaccharide gum; and (II) an inert pharmaceutical filler comprising up to about 80% by weight of the tablet; and (III) oxymorphone.

The term "heteropolysaccharide" as used herein is defined as a water-soluble polysaccharide containing two or more kinds of sugar units, the heteropolysaccharide having a branched or helical configuration, and having excellent water-wicking properties and immense thickening properties.

A preferred heteropolysaccharide is xanthan gum, which is a high molecular weight ($>10^6$) heteropolysaccharide. Other preferred heteropolysaecharides include derivatives of xanthan gum, such as deacylated xanthan gum, the carboxymethyl ether, and the propylene glycol ester.

The cross linking agents used in the controlled release embodiment of the present invention which are capable of cross-linking with the heteropolysaceharide include homopolysaccharide gums such as the galactomannans, i.e., polysaecharides which are composed solely of mannose and galactose. Galactomannans which have higher proportions of unsubstituted mannose regions have been found to achieve more interaction with the heteropolysaccharide. Locust bean gum, which has a higher ratio of mannose to the galactose, is especially preferred as compared to other galactomannans such as guar and hydroxypropyl guar.

Preferably, the ratio of heteropolysaccharide to homopolysaccharide is in the range of about 1:9 to about 9:1, preferably about 1:3 to about 3:1. Most preferably, the ratio of xanthan gum to polysaccharide material (i.e., locust bean gum, etc.) is preferably about 1:1.

In addition to the hydrophilic material, the controlled release delivery system can also contain an inert pharmaceutical diluent such as a monosaccharide, a disaccharide, a polyhydric alcohol and mixtures thereof. The ratio of diluent to hydrophilic matrix-forming material is generally in the range of about 1:3 to about 3:1.

The controlled release properties of the controlled release embodiment of the present invention may be optimized when the ratio of heteropolysaccharide gum to homopolysaccharide material is about 1:1, although heteropolysaccharide gum in an amount of from about 20 to about 80% or more by weight of the heterodisperse polysaccharide material provides an acceptable slow release product. The combination of any homopolysaccharide gums known to produce a synergistic effect when exposed to aqueous solutions may be used in accordance with the present invention. It is also possible that the type of synergism which is present with regard to the gum combination of the present invention could also occur between two homogeneous or two heteropolysaccharides. Other acceptable gelling agents which may be used in the present invention include those gelling agents well-known in the art. Examples include vegetable gums such as alginates, carrageenan, pectin, guar gum, xanthan gum, modified starch, hydroxypropylmethylcellulose, methylcellulose, and other cellulosic materials such as sodium carboxymethylcellulose and hydroxypropyl cellulose. This list is not meant to be exclusive.

The combination of xanthan gum with locust bean gum with or without the other homopolysaccharide gums is an especially preferred gelling agent. The chemistry of certain of the ingredients comprising the excipients of the present invention such as xanthan gum is such that the excipients are considered to be self-buffering agents which are substantially insensitive to the solubility of the medicament and likewise insensitive to the pH changes along the length of the gastrointestinal tract.

The inert filler of the sustained release excipient preferably comprises a pharmaceutically acceptable saccharide, including a monosaccharide, a disaccharide, or a polyhydric alcohol, and/or mixtures of any of the foregoing. Examples of suitable inert pharmaceutical fillers include sucrose, dextrose, lactose, microcrystalline cellulose, fructose, xylitol, sorbitol, mixtures thereof and the like. However, it is preferred that a soluble pharmaceutical filler such as lactose, dextrose, sucrose, or mixtures thereof be used.

The cationic cross-linking agent which is optionally used in conjunction with the controlled release embodiment of the present invention may be monovalent or multivalent metal cations. The preferred salts are the inorganic salts, including various alkali metal and/or alkaline earth metal sulfates, chlorides, borates, bromides, citrates, acetates, lactates, etc. Specific examples of suitable cationic cross-linking agents include calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate and sodium fluoride. Multivalent metal cations may also be utilized. However, the preferred cationic cross-linking agents are bivalent. Particularly preferred salts are calcium sulfate and sodium chloride. The cationic cross-linking agents of the present invention are added in an amount effective to obtain a desirable increased gel strength due to the cross-linking of the gelling agent (e.g., the heteropolysaccharide and homopolysaccharide gums). In preferred embodiments, the cationic cross-linking agent is included in the sustained release excipient of the present invention in an amount from about 1 to about 20% by weight of the sustained release excipient, and in an amount about 0.5% to about 16% by weight of the final dosage form.

In the controlled release embodiments of the present invention, the sustained release excipient comprises from about 10 to about 99% by weight of a gelling agent comprising a heteropolysaccharide gum and a homopolysaccharide gum, from about 1 to about 20% by weight of a cationic crosslinking agent, and from about 0 to about 89% by weight of an inert pharmaceutical diluent. In other embodiments, the sustained release excipient comprises from about 10 to about 75% gelling agent, from about 2 to about 15% cationic crosslinking agent, and from about 30 to about 75% inert diluent. In yet other embodiments, the sustained release excipient comprises from about 30 to about 75% gelling agent, from about 5 to about 10% cationic cross-linking agent, and from about 15 to about 65% inert diluent.

The sustained release excipient used in this embodiment of the present invention (with or without the optional cationic cross-linking agent) may be further modified by incorporation of a hydrophobic material which slows the hydration of the gums without disrupting the hydrophilic matrix. This is accomplished in preferred embodiments of the present invention by granulating the sustained release excipient with the solution or dispersion of a hydrophobic material prior to the incorporation of the medicament. The hydrophobic polymer may be selected from an alkylcellulose such as ethylcellulose, other hydrophobic cellulosic materials, polymers or copolymers derived from acrylic or methacrylic acid esters, copolymers of acrylic and methacrylic acid esters, zein, waxes, shellac, hydrogenated vegetable oils, and any other pharmaceutically acceptable hydrophobic material known to those skilled in the art. The amount of hydrophobic material incorporated into the sustained release excipient is that which is effective to slow the hydration of the gums without disrupting the hydrophilic matrix formed upon exposure to an environmental fluid. In certain preferred embodiments of the present invention, the hydrophobic material is included in the sustained release excipient in an amount from about 1 to about 20% by weight. The solvent for the hydrophobic material may be an aqueous or organic solvent, or mixtures thereof.

Examples of commercially available alkylcelluloses are Aquacoat coating (aqueous dispersion of ethylcellulose available from FMC of Philadelphia, Pa.) and Surelease coating (aqueous dispersion of ethylcellulose available from Colorcon of West Point, Pa.). Examples of commercially available acrylic polymers suitable for use as the hydrophobic material include Eudragit RS and RL polymers (copolymers of acrylic and methacrylic acid esters having a low content (e.g., 1:20 or 1:40) of quaternary ammonium compounds available from Rohm America of Piscataway, N.J.).

The controlled release matrix useful in the present invention may also contain a cationic cross-linking agent such as calcium sulfate in an amount sufficient to cross-link the gelling agent and increase the gel strength, and an inert hydrophobic material such as ethyl cellulose in an amount sufficient to slow the hydration of the hydrophilic material without disrupting it. Preferably, the controlled release delivery system is prepared as a pre-manufactured granulation.

EXAMPLES

Example 1

Two controlled release delivery systems are prepared by dry blending xanthan gum, locust bean gum, calcium sulfate dehydrate, and dextrose in a high speed mixed/granulator for 3 minutes. A slurry is prepared by mixing ethyl cellulose with alcohol. While running choppers/impellers, the slurry is added to the dry blended mixture, and granulated for another 3 minutes. The granulation is then dried to a LOD (loss on drying) of less than about 10% by weight. The granulation is then milled using 20 mesh screen. The relative quantities of the ingredients are listed in the table below.

TABLE 1

Controlled Release Delivery System

| Excipient | Formulation 1 (%) | Formulation 2 (%) |
|---|---|---|
| Locust Bean Gum, FCC | 25.0 | 30.0 |
| Xanthan Gum, NF | 25.0 | 30.0 |
| Dextrose, USP | 35.0 | 40.0 |
| Calcium Sulfate Dihydrate, NF | 10.0 | 0.0 |
| Ethylcellulose, NF | 5.0 | 0.0 |
| Alcohol, SD3A (Anhydrous)[1] | (10)[1] | (20.0)[1] |
| Total | 100.0 | 100.0 |

A series of tablets containing different amounts of oxymorphone hydrochloride were prepared using the controlled release delivery Formulation 1 shown in Table 1. The quantities of ingredients per tablet are as listed in the following table.

TABLE 2

Sample Tablets of Differing Strengths

| Component | Amount in Tablet (mg) | | | | |
|---|---|---|---|---|---|
| Oxymorphone HCl, USP (mg) | 5 | 10 | 20 | 40 | 80 |
| Controlled release delivery system | 160 | 160 | 160 | 160 | 160 |
| Silicified microcrystalline cellulose, N.F. | 20 | 20 | 20 | 20 | 20 |
| Sodium stearyl fumarate, NF | 2 | 2 | 2 | 2 | 2 |
| Total weight | 187 | 192 | 202 | 222 | 262 |
| Opadry (colored) | 7.48 | 7.68 | 8.08 | 8.88 | 10.48 |
| Opadry (clear) | 0.94 | 0.96 | 1.01 | 1.11 | 1.31 |

Examples 2 and 3

Two batches of 20 mg tablets were prepared as described above, using the controlled release delivery system of Formulation 1. One batch was formulated to provide relatively fast controlled release, the other batch was formulated to provide relatively slow controlled release. Compositions of the tablets are shown in the following table.

TABLE 3

Slow and Fast Release Compositions

| Ingredients | Example 2 Slow (mg) | Example 3 Fast (mg) | Example 4 Fast (mg) |
|---|---|---|---|
| Oxymorphone HCl, USP | 20 | 20 | 20 |
| Controlled Release Delivery System | 360 | 160 | 160 |
| Silicified Microcrystalline Cellulose, NF | 20 | 20 | 20 |
| Sodium stearyl fumarate, NF | 4 | 2 | 2 |
| Total weight | 404 | 202 | 202 |
| Coating (color or clear) | 12 | 12 | 9 |

The tablets of Examples 2, 3, and 4 were tested for in vitro release rate according to USP Procedure Drug Release USP 23. Release rate is a critical variable in attempting to control the blood plasma levels of oxymorphone and 6-hydroxyoxymorphone in a patient. Results are shown in the following Table 4.

TABLE 4

Release Rates of Slow and Fast Release Tablets

| Time (hr) | Example 2 (Slow Release) | Example 3 (Fast Release) | Example 4 (Fast Release) |
|---|---|---|---|
| 0.5 | 18.8 | 21.3 | 20.1 |
| 1 | 27.8 | 32.3 | 31.7 |
| 2 | 40.5 | 47.4 | 46.9 |
| 3 | 50.2 | 58.5 | 57.9 |
| 4 | 58.1 | 66.9 | 66.3 |
| 5 | 64.7 | 73.5 | 74.0 |
| 6 | 70.2 | 78.6 | 83.1 |
| 8 | 79.0 | 86.0 | 92.0 |
| 10 | 85.3 | 90.6 | 95.8 |
| 12 | 89.8 | 93.4 | 97.3 |

Clinical Studies

Three clinical studies were conducted to assess the bioavailability (rate and extent of absorption) of oxymorphone. Study 1 addressed the relative rates of absorption of controlled release (CR) oxymorphone tablets (of Examples 2 and 3) and oral oxymorphone solution in fasted patients. Study 2 addressed the relative rates of absorption of CR oxymorphone tablets (of Examples 2 and 3) and oral oxymorphone solution in fed patients. Study 3 addressed the relative rates of absorption of CR oxymorphone tablets (of Example 4) and oral oxymorphone solution in fed and fasted patients.

The blood plasma levels set forth herein as appropriate to achieve the objects of the present invention are mean blood plasma levels. As an example, if the blood plasma level of oxymorphone in a patient 12 hours after administration of a tablet is said to be at least 0.5 ng/ml, any particular individual, may have lower blood plasma levels after 12 hours. However, the mean minimum concentration should meet the limitation set forth. To determine mean parameters, a study should be performed with a minimum of 8 adult subjects, in a manner acceptable for filing an application for drug approval with the US Food and Drug Administration. In cases where large fluctuations are found among patients, further testing may be necessary to accurately determine mean values.

For all studies, the following procedures were followed, unless otherwise specified for a particular study.

The subjects were not to consume any alcohol-, caffeine-, or xanthine-containing foods or beverages for 24 hours prior to receiving study medication for each study period. Subjects were to be nicotine and tobacco free for at least 6 months prior to enrolling in the study. In addition, over-the-counter medications were prohibited 7 days prior to dosing and during the study. Prescription medications were not allowed 14 days prior to dosing and during the study.

Pharmacokinetic and Statistical Methods

The following pharmacokinetic parameters were computed from the plasma oxymorphone concentration-time data:

| | |
|---|---|
| $AUC_{(0-t)}$ | Area under the drug concentration-time curve from time zero to the time of the last quantifiable concentration (Ct), calculated using linear trapezoidal summation. |
| $AUC_{(0-inf)}$ | Area under the drug concentration-time curve from time zero to infinity. $AUC_{(0-inf)} = AUC_{(0-t)} + Ct/K_{el}$, where $K_{el}$ is the terminal elimination rate constant. |
| $AUC_{(0-24)}$ | Partial area under the drug concentration-time curve from time zero to 24 hours. |
| $C_{max}$ | Maximum observed drug concentration. |
| $T_{max}$ | Time of the observed maximum drug concentration. |
| $K_{el}$ | Elimination rate constant based on the linear regression of the terminal linear portion of the LN(concentration) time curve. |

Terminal elimination rate constants for use in the above calculations were in turn computed using linear regression of a minimum of three time points, at least two of which were consecutive. $K_{el}$ values for which correlation coefficients were less than or equal to 0.8 were not reported in the pharmacokinetic parameter tables or included in the statistical analysis. Thus $AUC_{(0-inf)}$ was also not reported in these cases.

A parametric (normal-theory) general linear model was applied to each of the above parameters (excluding $T_{max}$), and the LN-transformed parameters $C_{max}$, $AUC_{(0-24)}$, $AUC_{(0-t)}$, and $AUC_{(0-inf)}$. Initially, the analysis of variance (ANOVA) model included the following factors: treatment, sequence, subject within sequence, period, and carryover effect. If carryover effect was not significant, it was dropped from the model. The sequence effect was tested using the subject within sequence mean square, and all other main effects were tested using the residual error (error mean square).

Plasma oxymorphone concentrations were listed by subject at each collection time and summarized using descriptive statistics. Pharmacokinetic parameters were also listed by subject and summarized using descriptive statistics.

Study 1—Two Controlled Release Formulations; Fasted Patients

Healthy volunteers received a single oral dose of 20 mg CR oxymorphone taken with 240 ml water after a 10-hour fast. Subjects received the tablets of Example 2 (Treatment 1A) or Example 3 (Treatment 1B). Further subjects were given a single oral dose of 10 mg/10 ml oxymorphone solution in 180 ml apple juice followed with 60 ml water (Treatment 1C). The orally dosed solution was used to simulate an immediate release (IR) dose.

This study had a single-center, open-label, randomized, three-way crossover design using fifteen subjects. Subjects were in a fasted state following a 10-hour overnight fast. There was a 14-day washout interval between the three dose administrations. The subjects were confined to the clinic during each study period. Subjects receiving Treatment 1C were confined for 18 hours and subjects receiving Treatments 1A or 1B were confined for 48 hours after dosing. Ten-milliliter blood samples were collected during each study period at the 0 hour (predose), and at 0.5, 1, 1.5, 2, 3, 4, 5, 6, 7, 8, 10, 12, 14, 16, 18, 20, 24, 28, 32, 36, and 48 hours postdose for subjects receiving Treatment 1A or 1B and 0, 0.25, 0.5, 0.75, 1, 1.25, 1.5, 1.75, 2, 2.5, 3, 4, 5, 6, 7, 8, 10, 12, 14, 16, and 18 hours post-dose. The mean plasma concentration of oxymorphone versus time for each treatment across all subjects is shown in table 5.

TABLE 5

Mean Plasma Concentration vs. Time (ng/ml)

| Time (hr) | Treatment 1A | Treatment 1B | Treatment 1C |
|---|---|---|---|
| 0 | 0.000 | 0.000 | 0.0000 |
| 0.25 | | | 0.9489 |
| 0.5 | 0.2941 | 0.4104 | 1.3016 |
| 0.75 | | | 1.3264 |
| 1 | 0.5016 | 0.7334 | 1.3046 |
| 1.25 | | | 1.2041 |
| 1.5 | 0.5951 | 0.8192 | 1.0813 |
| 1.75 | | | 0.9502 |
| 2 | 0.6328 | 0.7689 | 0.9055 |
| 2.5 | | | 0.7161 |
| 3 | 0.5743 | 0.7341 | 0.6689 |
| 4 | 0.5709 | 0.6647 | 0.4879 |
| 5 | 0.7656 | 0.9089 | 0.4184 |
| 6 | 0.7149 | 0.7782 | 0.3658 |
| 7 | 0.6334 | 0.6748 | 0.3464 |
| 8 | 0.5716 | 0.5890 | 0.2610 |
| 10 | 0.4834 | 0.5144 | 0.2028 |
| 12 | 0.7333 | 0.6801 | 0.2936 |
| 14 | 0.6271 | 0.6089 | 0.2083 |
| 16 | 0.4986 | 0.4567 | 0.1661 |
| 18 | 0.4008 | 0.3674 | 0.1368 |
| 20 | 0.3405 | 0.2970 | |
| 24 | 0.2736 | 0.2270 | |
| 28 | 0.3209 | 0.2805 | |
| 32 | 0.2846 | 0.2272 | |
| 36 | 0.2583 | 0.1903 | |
| 48 | 0.0975 | 0.0792 | |

Figure 5:
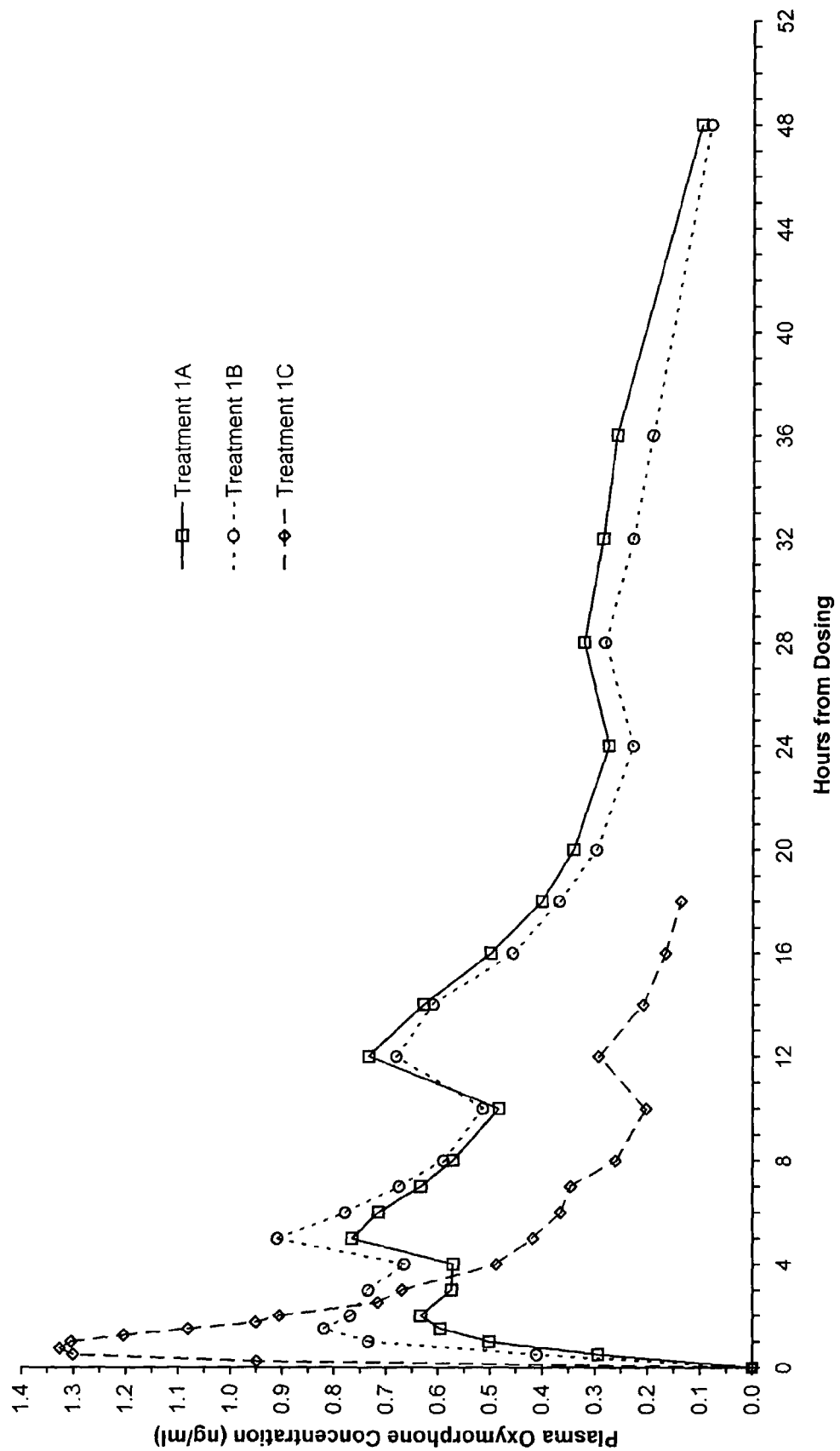
FIG. 5 is a graph of the mean blood plasma concentration of oxymorphone versus time for clinical study 1.

The results are shown graphically in FIG. 5. In both Table 5 and FIG. 5, the results are normalized to a 20 mg dosage. The immediate release liquid of Treatment 1C shows a classical curve, with a high and relatively narrow peak, followed by an exponential drop in plasma concentration. However, the controlled release oxymorphone tablets exhibit triple peaks in blood plasma concentration. The first peak occurs (on average) at around 3 hours. The second peak of the mean blood plasma concentration is higher than the first, occurring around 6-7 hours, on average).

Occasionally, in an individual, the first peak is higher than the second, although generally this is not the case. This makes it difficult to determine the time to maximum blood plasma concentration ($T_{max}$) because if the first peak is higher than the second, maximum blood plasma concentration ($C_{max}$) occurs much earlier (at around 3 hours) than in the usual case where the second peak is highest. Therefore, when we refer to the time to peak plasma concentration ($T_{max}$) unless otherwise specified, we refer to the time to the second peak. Further, when reference is made to the second peak, we refer to the time or blood plasma concentration at the point where the blood plasma concentration begins to drop the second time. Generally, where the first peak is higher than the second, the difference in the maximum blood plasma concentration at the two peaks is small. Therefore, this difference (if any) was ignored and the reported $C_{max}$ was the true maximum blood plasma concentration and not the concentration at the second peak.

TABLE 6

Pharmacokinetic Parameters of Plasma Oxymorphone for Study 1

|  | Treatment 1A | | Treatment 1B | | Treatment 1C | |
| --- | --- | --- | --- | --- | --- | --- |
|  | Mean | SD | Mean | SD | Mean | SD |
| $C_{max}$ | 0.8956 | 0.2983 | 1.0362 | 0.3080 | 2.9622 | 1.0999 |
| $T_{max}$ | 7.03 | 4.10 | 4.89 | 3.44 | 0.928 | 0.398 |
| $AUC_{(0-t)}$ | 17.87 | 6.140 | 17.16 | 6.395 | 14.24 | 5.003 |
| $AUC_{(0-inf)}$ | 19.87 | 6.382 | 18.96 | 6.908 | 16.99 | 5.830 |
| $T_{1/2el}$ | 10.9 | 2.68 | 11.4 | 2.88 | 6.96 | 4.61 |

Units: $C_{max}$ in ng/ml, $T_{max}$ in hours, AUC in ng*hr/ml, $T_{1/2el}$ in hours.

Relative bioavailability determinations are set forth in Tables 7 and 8. For these calculations, AUC was normalized for all treatments to a 20 mg dose.

TABLE 7

Relative Bioavailability ($F_{rel}$) Determination Based on $AUC_{(0-inf)}$

| $F_{rel}$ (1A vs. 1C) | $F_{rel}$ (1B vs. 1C) | $F_{rel}$ (1A vs. 1B) |
| --- | --- | --- |
| 1.193 ± 0.203 | 1.121 ± 0.211 | 1.108 ± 0.152 |

TABLE 8

Relative bioavailability Determination Based on $AUC_{(0-18)}$

| $F_{rel}$ (1A vs. 1C) | $F_{rel}$ (1B vs. 1C) | $F_{rel}$ (1A vs. 1B) |
| --- | --- | --- |
| 0.733 ± 0.098 | 0.783 ± 0.117 | 0.944 ± 0.110 |

Study 2—Two CR Formulations; Fed Patients

Healthy volunteers received a single oral dose of 20 mg CR oxymorphone taken with 240 ml water in a fed state. Subjects received the tablets of Example 2 (Treatment 2A) or Example 3 (Treatment 2B). Further subjects were given a single oral dose of 10 mg/10 ml oxymorphone solution in 180 ml apple juice followed with 60 ml water (Treatment 2C). The orally dosed solution was used to simulate an immediate release (IR) dose.

This study had a single-center, open-label, randomized, three-way crossover design using fifteen subjects. The subjects were in a fed state, after a 10-hour overnight fast followed by a standardized FDA high-fat breakfast. There was a 14-day washout interval between the three dose administrations. The subjects were confined to the clinic during each study period. Subjects receiving Treatment 2C were confined for 18 hours and subjects receiving Treatments 2A or 2B were confined for 48 hours after dosing. Ten-milliliter blood samples were collected during each study period at the 0 hour (predose), and at 0.5, 1, 1.5, 2, 3, 4, 5, 6, 7, 8, 10, 12, 14, 16, 18, 20, 24, 28, 32, 36, and 48 hours postdose for subjects receiving Treatment 2A or 2B and 0, 0.25, 0.5, 0.75, 1, 1.25, 1.5, 1.75, 2, 2.5, 3, 4, 5, 6, 7, 8, 10, 12, 14, 16, and 18 hours postdose. The mean plasma concentration of oxymorphone versus time for each treatment across all subjects is shown in table 9.

TABLE 9

Mean Plasma Concentration vs. Time (ng/ml)

| Time (hr) | Treatment 2A | Treatment 2B | Treatment 2C |
| --- | --- | --- | --- |
| 0 | 0.000 | 0.000 | 0.0000 |
| 0.25 |  |  | 1.263 |
| 0.5 | 0.396 | .0553 | 1.556 |
| 0.75 |  |  | 1.972 |
| 1 | 0.800 | 1.063 | 1.796 |
| 1.25 |  |  | 1.795 |
| 1.5 | 1.038 | 1.319 | 1.637 |
| 1.75 |  |  | 1.467 |
| 2 | 1.269 | 1.414 | 1.454 |
| 2.5 |  |  | 1.331 |
| 3 | 1.328 | 1.540 | 1.320 |
| 4 | 1.132 | 1.378 | 1.011 |
| 5 | 1.291 | 1.609 | 0.731 |
| 6 | 1.033 | 1.242 | 0.518 |
| 7 | 0.941 | 0.955 | 0.442 |
| 8 | 0.936 | 0.817 | 0.372 |
| 10 | 0.669 | 0.555 | 0.323 |
| 12 | 0.766 | 0.592 | 0.398 |
| 14 | 0.641 | 0.519 | 0.284 |
| 16 | 0.547 | 0.407 | 0.223 |
| 18 | 0.453 | 0.320 | 0.173 |
| 20 | 0.382 | 0.280 |  |
| 24 | 0.315 | 0.254 |  |
| 28 | 0.352 | 0.319 |  |
| 32 | 0.304 | 0.237 |  |
| 36 | 0.252 | 0.207 |  |
| 48 | 0.104 | 0.077 |  |

Figure 6:
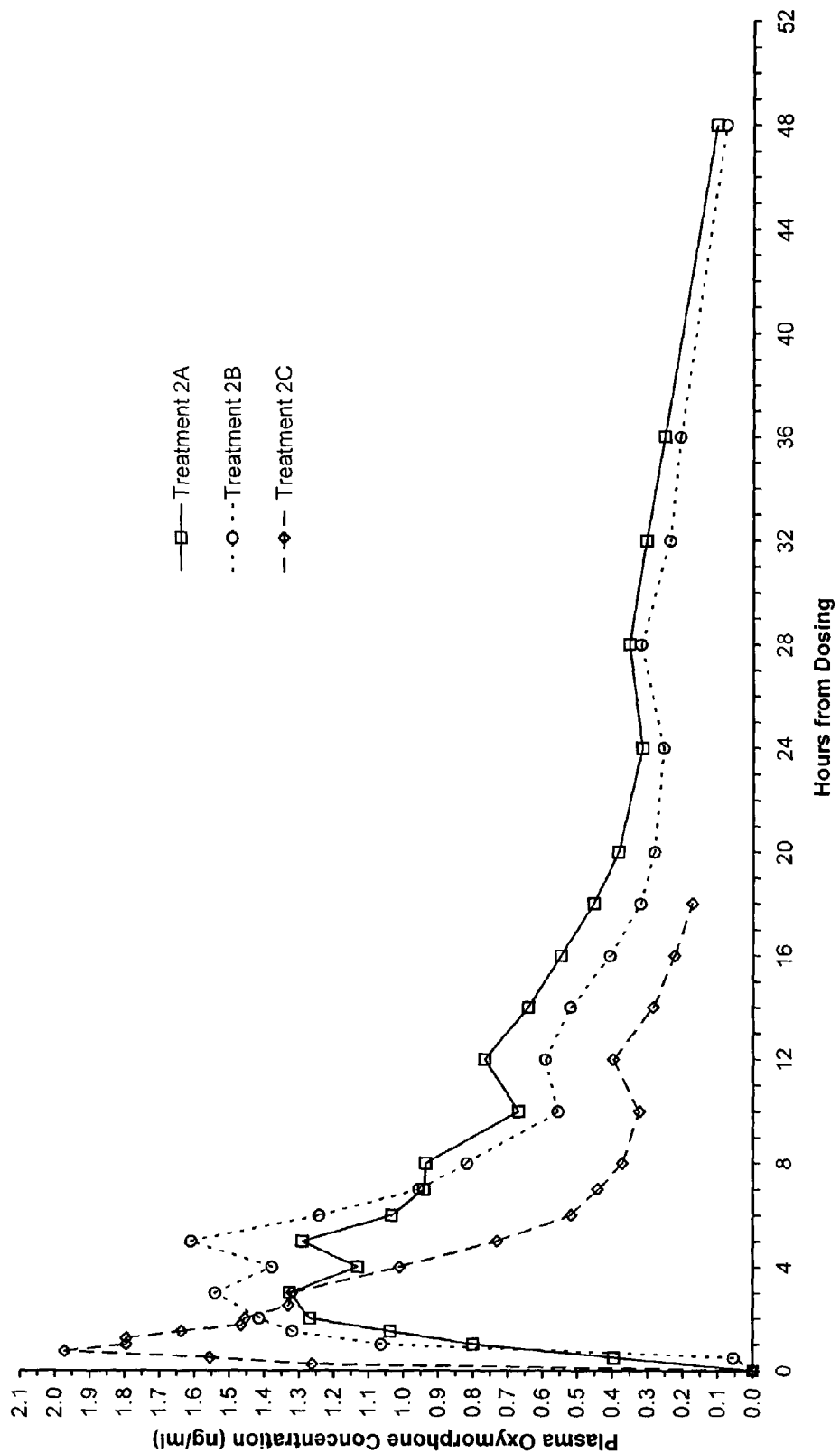
FIG. 6 is a graph of the mean blood plasma concentration of oxymorphone versus time for clinical study 2.

The results are shown graphically in FIG. 6. Again, the results have been normalized to a 20 mg dosage. As with Study 1, the immediate release liquid of Treatment 2C shows a classical curve, with a high and relatively narrow peak, followed by an exponential drop in plasma concentration, while the controlled release oxymorphone tablets exhibit triple peaks in blood plasma concentration. Thus, again when we refer to the time to peak plasma concentration ($T_{max}$) unless otherwise specified, we refer to the time to the second peak.

TABLE 10

Pharmacokinetic Parameters of Plasma Oxymorphone for Study 2

|  | Treatment 2A | | Treatment 2B | | Treatment 2C | |
| --- | --- | --- | --- | --- | --- | --- |
|  | Mean | SD | Mean | SD | Mean | SD |
| $C_{max}$ | 1.644 | 0.365 | 1.944 | 0.465 | 4.134 | 0.897 |
| $T_{max}$ | 3.07 | 1.58 | 2.93 | 1.64 | 0.947 | 0.313 |
| $AUC_{(0-t)}$ | 22.89 | 5.486 | 21.34 | 5.528 | 21.93 | 5.044 |
| $AUC_{(0-inf)}$ | 25.28 | 5.736 | 23.62 | 5.202 | 24.73 | 6.616 |
| $T_{1/2el}$ | 12.8 | 3.87 | 11.0 | 3.51 | 5.01 | 2.02 |

Units: $C_{max}$ in ng/ml, $T_{max}$ in hours, AUC in ng*hr/ml, $T_{1/2el}$ in hours.

In Table 10, the $T_{max}$ has a large standard deviation due to the two comparable peaks in blood plasma concentration. Relative bioavailability determinations are set forth in Tables 11 and 12.

TABLE 11

Relative Bioavailability Determination Based on $AUC_{(0-inf)}$

| $F_{rel}$ (2A vs. 2C) | $F_{rel}$ (2B vs. 2C) | $F_{rel}$ (2A vs. 2B) |
| --- | --- | --- |
| 1.052 ± 0.187 | 0.949 ± 0.154 | 1.148 ± 0.250 |

TABLE 12

Relative bioavailability Determination Based on AUC(0–18)

| $F_{rel}$ (2A vs. 2C) | $F_{rel}$ (2B vs. 2C) | $F_{rel}$ (2A vs. 2B) |
| --- | --- | --- |
| 0.690 ± 0.105 | 0.694 ± 0.124 | 1.012 ± 0.175 |

As may be seen from tables 5 and 10 and FIGS. 1 and 2, the $C_{max}$ for the CR tablets (treatments 1A, 1B, 2A and 2B) is considerably lower, and the $T_{max}$ much higher than for the immediate release oxymorphone. The blood plasma level of oxymorphone remains high well past the 8 (or even the 12) hour dosing interval desired for an effective controlled release tablet.

Study 3—One Controlled Release Formulation; Fed and Fasted Patients

This study had a single-center, open-label, analytically blinded, randomized, four-way crossover design. Subjects randomized to Treatment 3A and Treatment 3C, as described below, were in a fasted state following a 10-hour overnight fast. Subjects randomized to Treatment 3B and Treatment 3D, as described below, were in the fed state, having had a high fat meal, completed ten minutes prior to dosing. There was a 14-day washout interval between the four dose administrations. The subjects were confined to the clinic during each study period. Subjects assigned to receive Treatment 3A and Treatment 3B were discharged from the clinic on Day 3 following the 48-hour procedures, and subjects assigned to receive Treatment 3C and Treatment 3D were discharged from the clinic on Day 2 following the 36-hour procedures. On Day 1 of each study period the subjects received one of four treatments:

Treatments 3A and 3B: Oxymorphone controlled release 20 mg tablets from Example 3. Subjects randomized to Treatment 3A received a single oral dose of one 20 mg oxymorphone controlled release tablet taken with 240 ml of water after a 10-hour fasting period. Subjects randomized to Treatment 3B received a single oral dose of one 20 mg oxymorphone controlled release tablet taken with 240 ml of water 10 minutes after a standardized high fat meal.

Treatments 3C and 3D: oxymorphone HCl solution, USP, 1.5 mg/ml 10 ml vials. Subjects randomized to Treatment 3C received a single oral dose of 10 mg (6.7 ml) oxymorphone solution taken with 240 ml of water after a 10-hour fasting period. Subjects randomized to Treatment 3D received a single oral dose of 10 mg (6.7 ml) oxymorphone solution taken with 240 ml of water 10 minutes after a standardized high-fat meal.

A total of 28 male subjects were enrolled in the study, and 24 subjects completed the study. The mean age of the subjects was 27 years (range of 19 through 38 years), the mean height of the subjects was 69.6 inches (range of 64.0 through 75.0 inches), and the mean weight of the subjects was 169.0 pounds (range 117.0 through 202.0 pounds).

A total of 28 subjects received at least one treatment. Only subjects who completed all 4 treatments were included in the summary statistics and statistical analysis.

Blood samples (7 ml) were collected during each study period at the 0 hour (predose), and at 0.5, 1, 1.5, 2, 3, 4, 5, 6, 8, 10, 12, 14, 16, 20, 24, 30, 36, and 48 hours post-dose (19 samples) for subjects randomized to Treatment 3A and Treatment 3B. Blood samples (7 ml) were collected during each study period at the 0 hour (predose), and at 0.25, 0.5, 0.75, 1, 1.25, 1.5, 1.75, 2, 3, 4, 5, 6, 8, 10, 12, 14, 16, 20, and 36 hours post-dose (21 samples) for subjects randomized to Treatment 3C and Treatment 3D.

Figure 7:
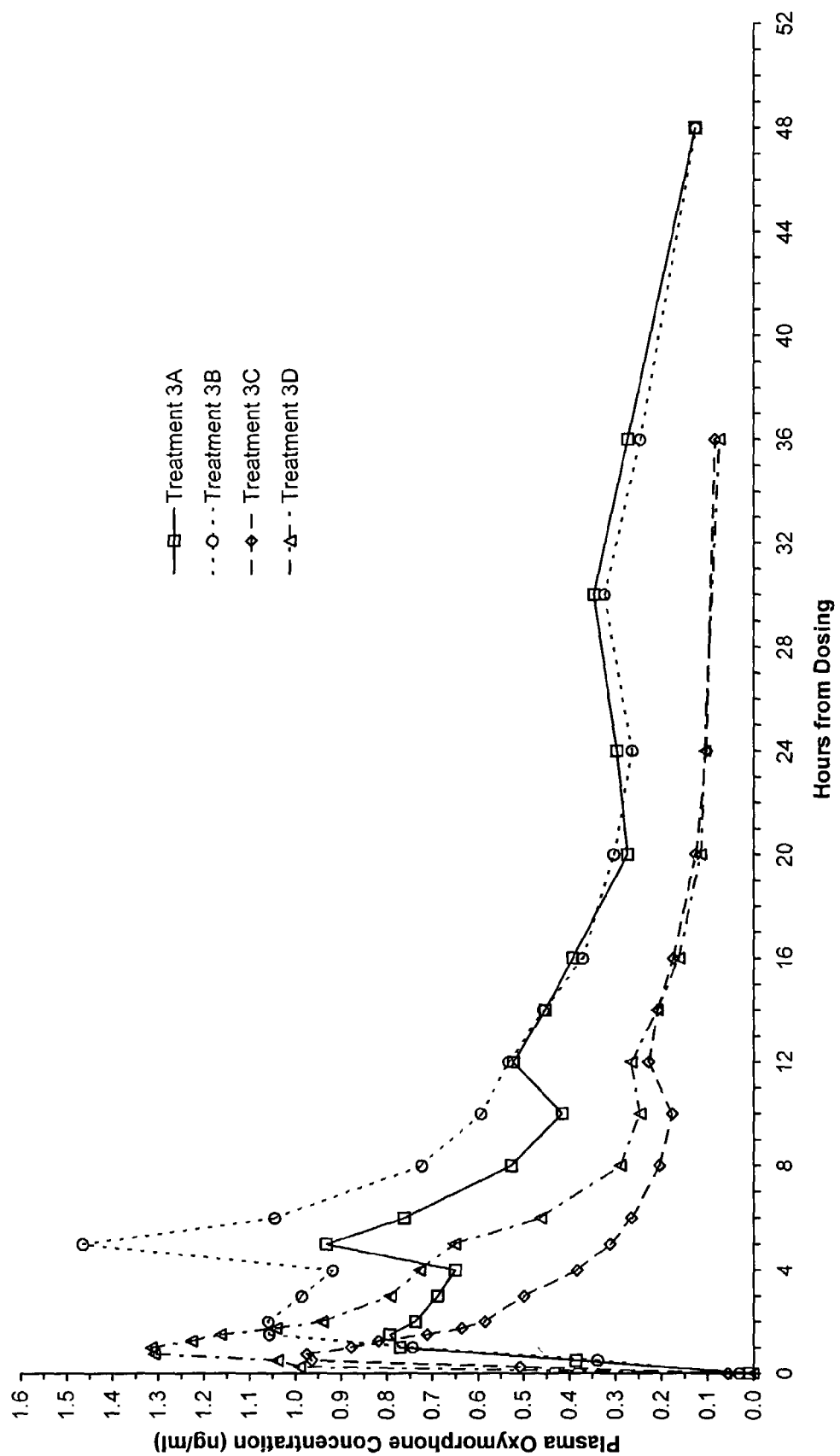
FIG. 7 is a graph of the mean blood plasma concentration of oxymorphone versus time for clinical study 3.

The mean oxymorphone plasma concentration versus time curves for Treatments 3A, 3B, 3C, and 3D are presented in FIG. 7. The results have been normalized to a 20 mg dosage. The data is contained in Table 13. The arithmetic means of the plasma oxymorphone pharmacokinetic parameters and the statistics for all Treatments are summarized in Table 1.

TABLE 13

Mean Plasma Concentration vs. Time (ng/ml)

| Time (hr) | Treatment 3A | Treatment 3B | Treatment 3C | Treatment 3D |
| --- | --- | --- | --- | --- |
| 0 | 0.0084 | 0.0309 | 0.0558 | 0.0000 |
| 0.25 |  |  | 0.5074 | 0.9905 |
| 0.5 | 0.3853 | 0.3380 | 0.9634 | 1.0392 |
| 0.75 |  |  | 0.9753 | 1.3089 |
| 1 | 0.7710 | 0.7428 | 0.8777 | 1.3150 |
| 1.25 |  |  | 0.8171 | 1.2274 |
| 1.5 | 0.7931 | 1.0558 | 0.7109 | 1.1638 |
| 1.75 |  |  | 0.6357 | 1.0428 |
| 2 | 0.7370 | 1.0591 | 0.5851 | 0.9424 |
| 3 | 0.6879 | 0.9858 | 0.4991 | 0.7924 |
| 4 | 0.6491 | 0.9171 | 0.3830 | 0.7277 |
| 5 | 0.9312 | 1.4633 | 0.3111 | 0.6512 |
| 6 | 0.7613 | 1.0441 | 0.2650 | 0.4625 |
| 8 | 0.5259 | 0.7228 | 0.2038 | 0.2895 |
| 10 | 0.4161 | 0.5934 | 0.1768 | 0.2470 |
| 12 | 0.5212 | 0.5320 | 0.2275 | 0.2660 |
| 14 | 0.4527 | 0.4562 | 0.2081 | 0.2093 |
| 16 | 0.3924 | 0.3712 | 0.1747 | 0.1623 |
| 20 | 0.2736 | 0.3021 | 0.1246 | 0.1144 |
| 24 | 0.2966 | 0.2636 | 0.1022 | 0.1065 |
| 30 | 0.3460 | 0.3231 |  |  |
| 36 | 0.2728 | 0.2456 | 0.0841 | 0.0743 |
| 48 | 0.1263 | 0.1241 |  |  |

TABLE 14

Pharmacokinetic Parameters of Plasma Oxymorphone for Study 3

|  | Treatment 3A | | Treatment 3B | | Treatment 3C | | Treatment 3D | |
|---|---|---|---|---|---|---|---|---|
|  | Mean | SD | Mean | SD | Mean | SD | Mean | SD |
| $C_{max}$ | 1.7895 | 0.6531 | 1.1410 | 0.4537 | 2.2635 | 1.0008 | 2.2635 | 1.0008 |
| $T_{max}$ | 5.65 | 9.39 | 5.57 | 7.14 | 0.978 | 1.14 | 0.978 | 1.14 |
| $AUC_{(0-t)}$ | 14.27 | 4.976 | 11.64 | 3.869 | 12.39 | 4.116 | 12.39 | 4.116 |
| $AUC_{(0-inf)}$ | 19.89 | 6.408 | 17.71 | 8.471 | 14.53 | 4.909 | 14.53 | 4.909 |
| $T_{1/2el}$ | 21.29 | 6.559 | 19.29 | 5.028 | 18.70 | 6.618 | 18.70 | 6.618 |
|  | 12.0 | 3.64 | 12.3 | 3.99 | 16.2 | 11.4 | 16.2 | 11.4 |

The relative bioavailability calculations are summarized in tables 15 and 16.

TABLE 15

Relative Bioavailability Determination Based on $AUC_{(0-inf)}$

| $F_{rel}$ (3A vs. 3C) | $F_{rel}$ (3B vs. 3D) | $F_{rel}$ (3D vs. 3C) | $F_{rel}$ (3A vs. 3B) |
|---|---|---|---|
| 1.040 ± 0.1874 | 0.8863 ± 0.2569 | 1.368 ± 0.4328 | 1.169 ± 0.2041 |

TABLE 16

Relative bioavailability Determination Based on $AUC_{(0-24)}$

| $F_{rel}$ (3A vs. 2C) | $F_{rel}$ (3B vs. 3D) | $F_{rel}$ (3D vs. 3C) | $F_{rel}$ (3A vs. 3B) |
|---|---|---|---|
| 0.9598 ± 0.2151 | 0.8344 ± 0.100 | 1.470 ± 0.3922 | 1.299 ± 0.4638 |

The objectives of this study were to assess the relative bioavailability of oxymorphone from oxymorphone controlled release (20 mg) compared to oxymorphone oral solution (10 mg) under both fasted and fed conditions, and to determine the effect of food on the bioavailability of oxymorphone from the controlled release formulation, oxymorphone CR, and from the oral solution.

The presence of a high fat meal had a substantial effect on the oxymorphone $C_{max}$, but less of an effect on oxymorphone AUC from oxymorphone controlled release tablets. Least Squares (LS) mean $C_{max}$ was 58% higher and LS mean $AUC_{(0-t)}$ and $AUC_{(0-inf)}$ were 18% higher for the fed condition (Treatment B) compared to the fasted condition (Treatment A) based on LN-transformed data. This was consistent with the relative bioavailability determination from $AUC_{(0-inf)}$ since mean $F_{rel}$ was 1.17. Mean $T_{max}$ values were similar (approximately 5.6 hours), and no significant different in $T_{max}$ was shown using nonparametric analysis. Half value durations were significantly different between the two treatments.

The effect of food on oxymorphone bioavailability from the oral solution was more pronounced, particularly in terms of AUC. LS mean $C_{max}$ was 50% higher and LS mean $AUC_{(0-t)}$ and $AUC_{(0-inf)}$ were 32-34% higher for the fed condition (Treatment D) compared to the fasted condition (Treatment C) based on LN-transformed data. This was consistent with the relative bioavailability determination from $AUC_{(0-inf)}$ since mean $F_{rel}$ was 1.37. Mean $T_{max}$ (approximately 1 hour) was similar for the two treatments and no significant difference was shown.

Under fasted conditions, oxymorphone controlled release 20 mg tablets exhibited similar extent of oxymorphone availability compared to 10 mg oxymorphone oral solution normalized to a 20 mg dose (Treatment A versus Treatment C). From LN-transformed data, LS mean $AUC_{(0-t)}$ was 17% higher for oxymorphone CR, whereas LS mean $AUC_{(0-inf)}$ values were nearly equal (mean ratio=99%). Mean $F_{rel}$ values calculated from $AUC_{(0-inf)}$ and $AUC_{(0-24)}$, (1.0 and 0.96, respectively) also showed similar extent of oxymorphone availability between the two treatments.

As expected, there were differences in parameters reflecting rate of absorption. LS mean $C_{max}$ was 49% lower for oxymorphone controlled release tablets compared to the dose-normalized oral solution, based on LN-transformed data. Half-value duration was significantly longer for the controlled release formulation (means, 12 hours versus 2.5 hours).

Under fed conditions, oxymorphone availability from oxymorphone controlled release 20 mg was similar compared to 10 mg oxymorphone oral solution normalized to a 20 mg dose (Treatment B versus Treatment D). From LN-transformed data, LS mean $AUC_{(0-inf)}$ was 12% lower for oxymorphone CR. Mean $F_{rel}$ values calculated from $AUC_{(0-inf)}$ and $AUC_{(0-24)}$, (0.89 and 0.83 respectively) also showed similar extent of oxymorphone availability from the tablet. As expected, there were differences in parameters reflecting rate of absorption. LS mean $C_{max}$ was 46% lower for oxymorphone controlled release tablets compared to the dose-normalized oral solution, based on LN-transformed data. Mean $T_{max}$ was 5.7 hours for the tablet compared to 1.1 hours for the oral solution. Half-value duration was significantly longer for the controlled release formulation (means, 7.8 hours versus 3.1 hours).

The presence of a high fat meal did not appear to substantially affect the availability following administration of oxymorphone controlled release tablets. LS mean ratios were 97% for $AUC_{(0-t)}$ and 91% for $C_{max}$ (Treatment B versus A), based on LN-transformed data. This was consistent with the relative bioavailability determination from $AUC_{(0-24)}$, since mean $F_{rel}$ was 0.97. Mean $T_{max}$ was later for the fed treatment compared to the fasted treatment (5.2 and 3.6 hours, respectively), and difference was significant.

Under fasted conditions, oxymorphone controlled release 20 mg tablets exhibited similar availability compared to 10 mg oxymorphone oral solution normalized to a 20 mg dose (Treatment A versus Treatment C). From LN-transformed data, LS mean ratio for $AUC_{(0-t)}$ was 104.5%. Mean $F_{rel}$ (0.83) calculated from $AUC_{(0-24)}$ also showed similar extent of oxymorphone availability between the two treatments. Mean $T_{max}$ was 3.6 hours for the tablet compared to 0.88 for the oral solution. Half-value duration was significantly longer for the controlled release formulation (means, 11 hours versus 2.2 hours).

Under fed conditions, availability from oxymorphone controlled release 20 mg was similar compared to 10 mg oxymorphone oral solution normalized to a 20 mg dose (Treatment B versus Treatment D). From LN-transformed data, LS mean $AUC_{(0-t)}$ was 14% higher for oxymorphone CR. Mean $F_{rel}$ (0.87) calculated from $AUC_{(0-24)}$ also indicated similar extent of availability between the treatments. Mean $T_{max}$ was 5.2 hours for the tablet compared to 1.3 hour for the oral solution. Half-value duration was significantly longer for the controlled release formulation (means, 14 hours versus 3.9 hours).

The extent of oxymorphone availability from oxymorphone controlled release 20 mg tablets was similar under fed and fasted conditions since there was less than a 20% difference in LS mean $AUC_{(0-t)}$ and $AUC_{(0-inf)}$ values for each treatment, based on LN-transformed data. $T_{max}$ was unaffected by food; however, LS mean $C_{max}$ was increased 58% in the presence of the high fat meal. Both rate and extent of oxymorphone absorption from the oxymorphone oral solution were affected by food since LS mean $C_{max}$ and AUC values were increased approximately 50 and 30%, respectively. $T_{max}$ was unaffected by food. Under both fed and fasted conditions, oxymorphone controlled release tablets exhibited similar extent of oxymorphone availability compared to oxymorphone oral solution since there was less than a 20% difference in LS mean AUC(0-t) and AUC(0-inf) values for each treatment.

Bioavailability following oxymorphone controlled release 20 mg tablets was also similar under fed and fasted conditions since there was less than a 20% difference in LS mean $C_{max}$ and AUC values for each treatment. $T_{max}$ was later for the fed condition. The presence of food did not affect the extent of availability from oxymorphone oral solution since LS mean AUC values were less than 20% different. However, $C_{max}$ was decreased 35% in the presence of food. $T_{max}$ was unaffected by food. Under both fed and fasted conditions, oxymorphone controlled release tablets exhibited similar extent of availability compared to oxymorphone oral solution since there was less than a 20% difference in LS mean AUC values for each treatment.

Figure 8:
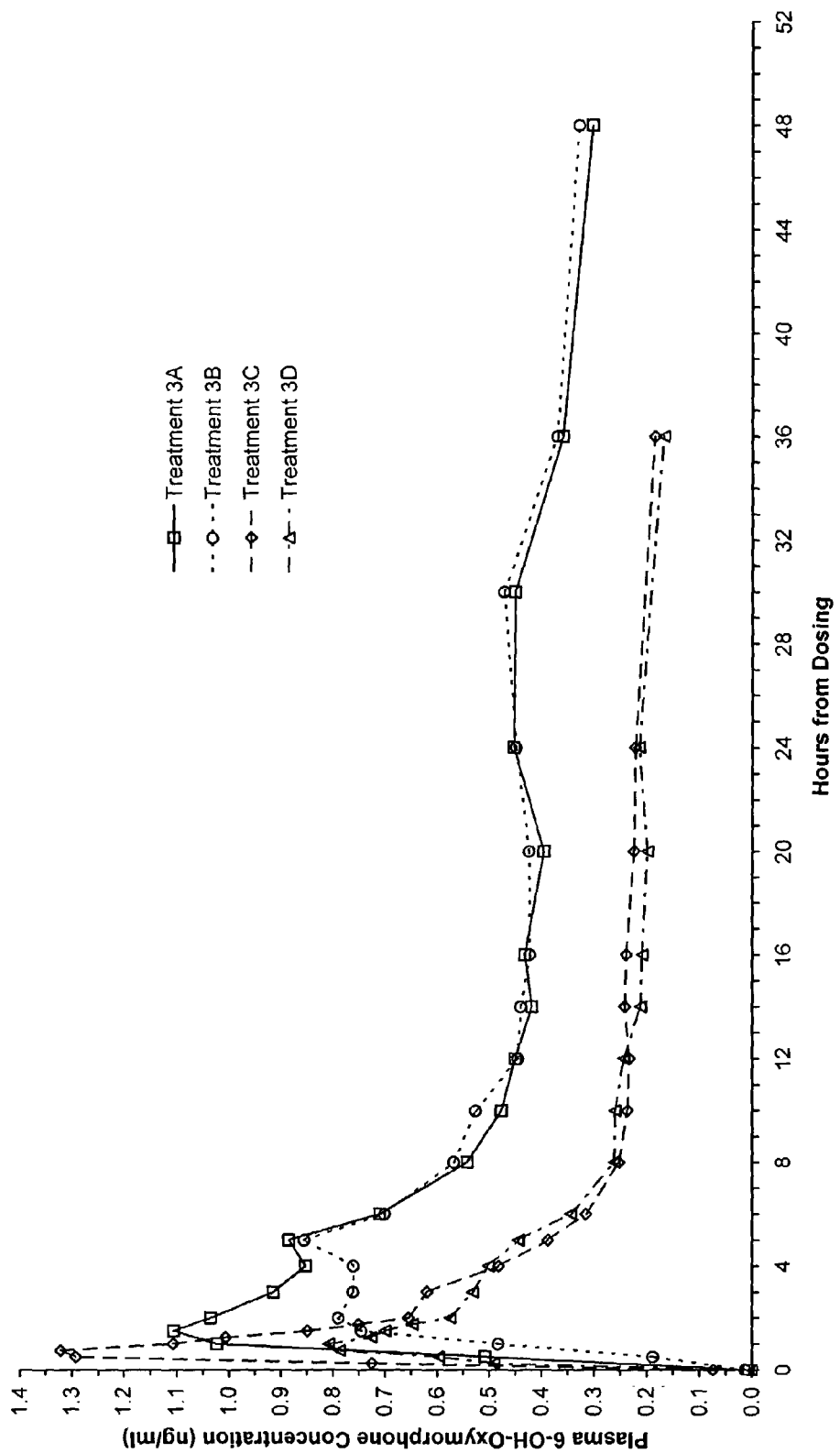
FIG. 8 is a graph of the mean blood plasma concentration of 6-hydroxy oxymorphone versus time for clinical study 3.

The mean 6-OH oxymorphone plasma concentration versus time curves for Treatments 3A, 3B, 3C, and 3D are presented in FIG. 8. The data is contained in Table 17.

TABLE 17

Mean Plasma Concentration vs. Time (ng/ml)

6-Hydroxyoxymorphone

| Time (hr) | Treatment 3A | Treatment 3B | Treatment 3C | Treatment 3D |
|---|---|---|---|---|
| 0 | 0.0069 | 0.0125 | 0.0741 | 0.0000 |
| 0.25 | | | 0.7258 | 0.4918 |
| 0.5 | 0.5080 | 0.1879 | 1.2933 | 0.5972 |
| 0.75 | | | 1.3217 | 0.7877 |
| 1 | 1.0233 | 0.4830 | 1.1072 | 0.8080 |
| 1.25 | | | 1.0069 | 0.7266 |
| 1.5 | 1.1062 | 0.7456 | 0.8494 | 0.7001 |
| 1.75 | | | 0.7511 | 0.6472 |
| 2 | 1.0351 | 0.7898 | 0.6554 | 0.5758 |
| 3 | 0.9143 | 0.7619 | 0.6196 | 0.5319 |
| 4 | 0.8522 | 0.7607 | 0.4822 | 0.5013 |
| 5 | 0.8848 | 0.8548 | 0.3875 | 0.4448 |
| 6 | 0.7101 | 0.7006 | 0.3160 | 0.3451 |
| 8 | 0.5421 | 0.5681 | 0.2525 | 0.2616 |
| 10 | 0.4770 | 0.5262 | 0.2361 | 0.2600 |
| 12 | 0.4509 | 0.4454 | 0.2329 | 0.2431 |
| 14 | 0.4190 | 0.4399 | 0.2411 | 0.2113 |
| 16 | 0.4321 | 0.4230 | 0.2385 | 0.2086 |
| 20 | 0.3956 | 0.4240 | 0.2234 | 0.1984 |
| 24 | 0.4526 | 0.4482 | 0.2210 | 0.2135 |
| 30 | 0.4499 | 0.4708 | | |
| 36 | 0.3587 | 0.3697 | 0.1834 | 0.1672 |
| 48 | 0.3023 | 0.3279 | | |

TABLE 18

Pharmacokinetic Parameters of Plasma Oxymorphone for Study 3

| | Treatment 3A | | Treatment 3B | | Treatment 3C | | Treatment 3D | |
|---|---|---|---|---|---|---|---|---|
| | Mean | SD | Mean | SD | Mean | SD | Mean | SD |
| $C_{max}$ | 1.2687 | 0.5792 | 1.1559 | 0.4848 | 1.5139 | 0.7616 | 0.9748 | 0.5160 |
| $T_{max}$ | 3.61 | 7.17 | 5.20 | 9.52 | 0.880 | 0.738 | 1.30 | 1.04 |
| $AUC_{(0-t)}$ | 22.47 | 10.16 | 22.01 | 10.77 | 10.52 | 4.117 | 9.550 | 4.281 |
| $AUC_{(0-inf)}$ | 38.39 | 23.02 | 42.37 | 31.57 | 20.50 | 7.988 | 23.84 | 11.37 |
| $T_{½el}$ | 39.1 | 36.9 | 39.8 | 32.6 | 29.3 | 12.0 | 44.0 | 35.00 |

Study 4—Controlled Release 20 mg vs Immediate Release 10 mg

A study was conducted to compare the bioavailability and pharmacokinetics of controlled release and immediate release oxymorphone tablets under single-dose and multiple-dose (steady state) conditions. For the controlled release study, healthy volunteers received a single dose of a 20 mg controlled release oxymorphone table on the morning of Day 1. Beginning on the morning of Day 3, the volunteers were administered a 20 mg controlled release oxymorphone tablet every 12 hours through the morning dose of Day 9. For the immediate release study, healthy volunteers received a single 10 mg dose of an immediate release oxymorphone tablet on the morning of Day 1. On the morning of Day 3, additional 10 mg immediate release tablets were administered every six hours through the first two doses on Day 9.

Figure 9:
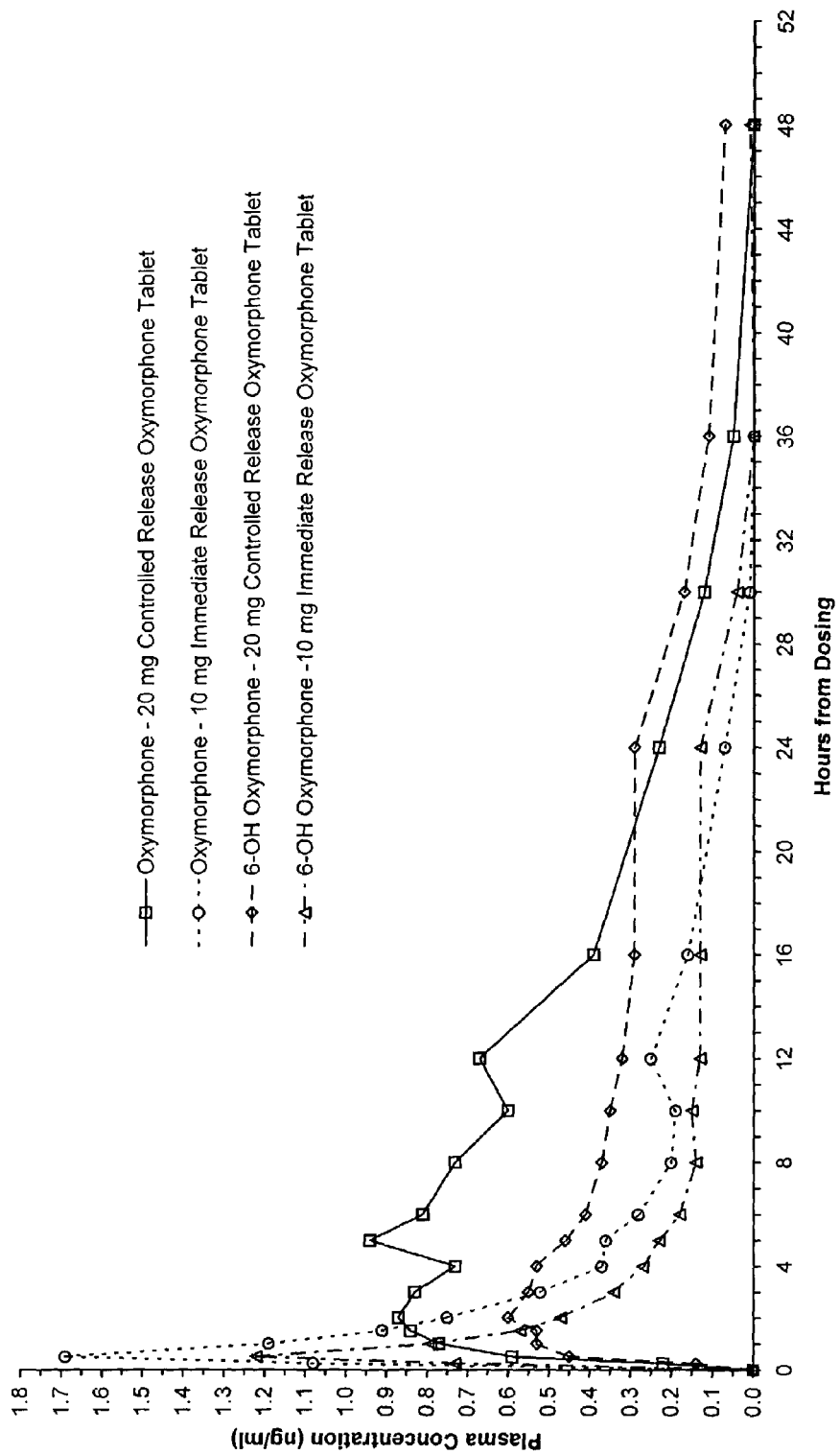
FIG. 9 is a graph of the mean blood plasma concentration of oxymorphone for immediate and controlled release tablets from a single dose study.

FIG. 9 shows the average plasma concentrations of oxymorphone and 6-6-hydroxy oxymorphone for all subjects after a single dose either controlled release (CR) 20 mg or immediate release (IR) 10 mg oxymorphone. The data in the figure (as with the other relative experimental data herein) is normalized to a 20 mg dose. The immediate release tablet shows a classical curve, with a high, relatively narrow peak followed by an exponential drop in plasma concentration. The controlled release oxymorphone tablets show a lower peak with extended moderate levels of oxymorphone and 6-hydroxy oxymorphone. Table 19 shows the levels of oxymorphone and 6-hydroxy oxymorphone from FIG. 9 in tabular form.

TABLE 19

Mean Plasma Concentration (ng/ml)

| | Oxymorphone | | 6-Hydroxyoxymorphone | |
|---|---|---|---|---|
| Hour | Controlled Release 20 mg | Immediate Release 10 mg | Controlled Release 20 mg | Immediate Release 10 mg |
| 0.00 | 0.00 | 0.00 | 0.00 | 0.00 |
| 0.25 | 0.22 | 1.08 | 0.14 | 0.73 |
| 0.50 | 0.59 | 1.69 | 0.45 | 1.22 |
| 1.00 | 0.77 | 1.19 | 0.53 | 0.79 |
| 1.50 | 0.84 | 0.91 | 0.53 | 0.57 |
| 2.00 | 0.87 | 0.75 | 0.60 | 0.47 |
| 3.00 | 0.83 | 0.52 | 0.55 | 0.34 |
| 4.00 | 0.73 | 0.37 | 0.53 | 0.27 |
| 5.00 | 0.94 | 0.36 | 0.46 | 0.23 |
| 6.00 | 0.81 | 0.28 | 0.41 | 0.18 |
| 8.00 | 0.73 | 0.20 | 0.37 | 0.14 |
| 10.0 | 0.60 | 0.19 | 0.35 | 0.15 |
| 12.0 | 0.67 | 0.25 | 0.32 | 0.13 |
| 16.0 | 0.39 | 0.16 | 0.29 | 0.13 |
| 24.0 | 0.23 | 0.07 | 0.29 | 0.13 |
| 30.0 | 0.12 | 0.01 | 0.17 | 0.04 |
| 36.0 | 0.05 | 0.00 | 0.11 | 0.00 |
| 48.0 | 0.00 | 0.00 | 0.07 | 0.01 |

Figure 10:
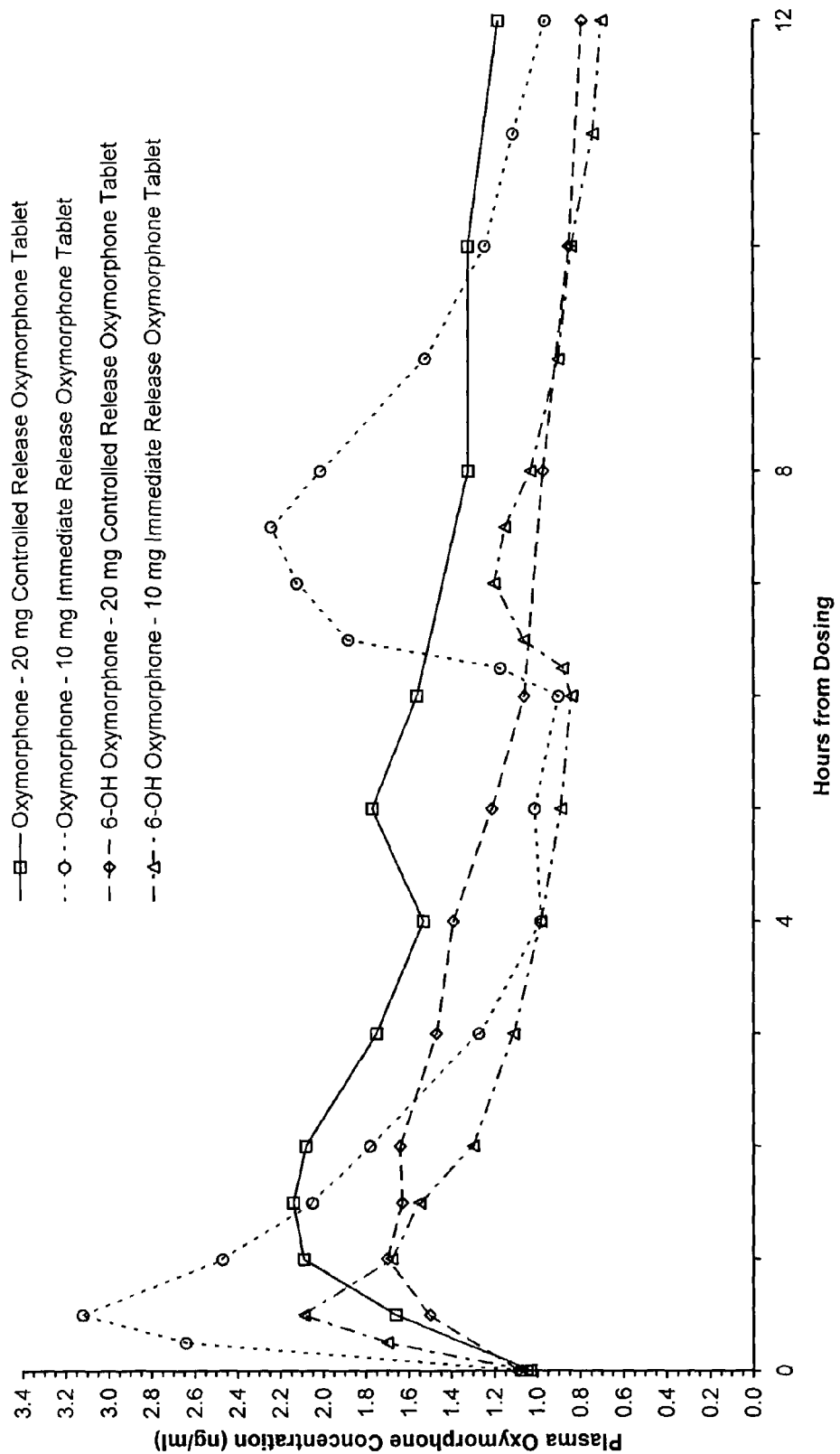
FIG. 10 is a graph of the mean blood plasma concentration of oxymorphone for immediate and controlled release tablets from a steady state study.

FIG. 10 shows the average plasma concentrations of oxymorphone and 6-hydroxyoxymorphone for all subjects in the steady state test, for doses of controlled release 20 mg tablets and immediate release 10 mg tablets of oxymorphone. The figure shows the plasma concentrations after the final controlled release tablet is given on Day 9, and the final immediate release tablet is given 12 hours thereafter. The steady state administration of the controlled release tablets clearly shows a steady moderate level of oxymorphone ranging from just over 1 ng/ml to almost 1.75 ng/ml over the course of a twelve hour period, where the immediate release tablet shows wide variations in blood plasma concentration. Table 20 shows the levels of oxymorphone and 6-hydroxyoxymorphone from FIG. 10 in tabular form.

TABLE 20

Summary of Mean Plasma Concentration (ng/ml)

| | | Oxymorphone | | 6-Hydroxyoxymorphone | |
|---|---|---|---|---|---|
| Day | Hour | Controlled Release 20 mg | Immediate Release 10 mg | Controlled Release 20 mg | Immediate Release 10 mg |
| 4 | 0.00 | 1.10 | 0.75 | 0.89 | 0.72 |
| 5 | 0.00 | 1.12 | 0.84 | 1.15 | 0.88 |
| 6 | 0.00 | 1.20 | 0.92 | 1.15 | 0.87 |
| 7 | 0.00 | 1.19 | 0.91 | 1.27 | 1.00 |
| 8 | 0.00 | 1.19 | 0.86 | 1.29 | 0.98 |
| 9 | 0.00 | 1.03 | 1.07 | 1.09 | 1.05 |
| | 0.25 | | 2.64 | | 1.70 |
| | 0.50 | | 3.12 | 1.50 | 2.09 |
| | 1.00 | | 2.47 | 1.70 | 1.68 |
| | 1.50 | | 2.05 | 1.63 | 1.55 |
| | 2.00 | | 1.78 | 1.64 | 1.30 |
| | 3.00 | | 1.27 | 1.47 | 1.11 |
| | 4.00 | | 0.98 | 1.39 | 0.98 |
| | 5.00 | | 1.01 | 1.21 | 0.89 |

TABLE 20-continued

Summary of Mean Plasma Concentration (ng/ml)

| | | Oxymorphone | | 6-Hydroxyoxymorphone | |
|---|---|---|---|---|---|
| Day | Hour | Controlled Release 20 mg | Immediate Release 10 mg | Controlled Release 20 mg | Immediate Release 10 mg |
| | 6.00 | | 0.90 | 1.06 | 0.84 |
| | 6.25 | | 1.17 | | 0.88 |
| | 6.50 | | 1.88 | | 1.06 |
| | 7.00 | | 2.12 | | 1.20 |
| | 7.50 | | 2.24 | | 1.15 |
| | 8.00 | 1.32 | 2.01 | 0.97 | 1.03 |
| | 9.00 | | 1.52 | | 0.90 |
| | 10.0 | 1.32 | 1.24 | 0.85 | 0.84 |
| | 11.0 | | 1.11 | | 0.74 |
| | 12.0 | 1.18 | 0.96 | 0.79 | 0.70 |

TABLE 21

Mean Single-Dose Pharmacokinetic Results

| | Controlled Release 20 mg | | Immediate Release 10 mg | |
|---|---|---|---|---|
| | oxymorphone | 6-OH-oxymorphone | oxymorphone | 6-OH-oxymorphone |
| $AUC_{(o-t)}$ | 14.74 | 11.54 | 7.10 | 5.66 |
| $AUC_{(o-inf)}$ | 15.33 | 16.40 | 7.73 | 8.45 |
| $C_{max}$ (ng/ml) | 1.12 | 0.68 | 1.98 | 1.40 |
| $T_{max}$ (hr) | 5.00 | 2.00 | 0.50 | 0.50 |
| T½ (hr) | 9.25 | 26.09 | 10.29 | 29.48 |

Parent 6-OH oxymorphone $AUC_{(o-t)}$ values were lower than the parent compound after administration of either dosage form, but the $AUC_{(o-inf)}$ values are slightly higher due to the longer half-life for the metabolite. This relationship was similar for both the immediate-release (IR) and controlled release (CR) dosage forms. As represented by the average plasma concentration graph, the CR dosage form has a significantly longer time to peak oxymorphone concentration and a lower peak oxymorphone concentration. The 6-OH oxymorphone peak occurred sooner than the parent peak following the CR dosage form, and simultaneously with the parent peak following the IR dosage form.

It is important to note that while the present invention is described and exemplified using 20 mg tablets, the invention may also be used with other strengths of tablets. In each strength, it is important to note how a 20 mg tablet of the same composition (except for the change in strength) would act. The blood plasma levels and pain intensity information are provided for 20 mg tablets, however the present invention is also intended to encompass 5 to 80 mg controlled release tablets. For this reason, the blood plasma level of oxymorphone or 6-hydroxyoxymorphone in nanograms per milliliter of blood, per mg oxymorphone (ng/mg·ml) administered is measured. Thus at 0.02 ng/mg·ml, a 5 mg tablet should produce a minimum blood plasma concentration of 0.1 ng/ml. A stronger tablet will produce a higher blood plasma concentration of active molecule, generally proportionally. Upon administration of a higher dose tablet, for example 80 mg, the blood plasma level of oxymorphone and 6-OH oxymorphone may more than quadruple compared to a 20 mg dose, although conventional treatment of low bioavailability substances would lead away from this conclusion. If this is the case, it may be because the body can only process a limited amount oxymorphone at one time. Once the bolus is processed, the blood level of oxymorphone returns to a proportional level.

It is the knowledge that controlled release oxymorphone tablets are possible to produce and effective to use, which is most important, made possible with the high bioavailability of oxymorphone in a controlled release tablet. This also holds true for continuous periodic administration of controlled release formulations. The intent of a controlled release opioid formulation is the long-term management of pain. Therefore, the performance of a composition when administered periodically (one to three times per day) over several days is important. In such a regime, the patient reaches a "steady state" where continued administration will produce the same results, when measured by duration of pain relief and blood plasma levels of pharmaceutical. Such a test is referred to as a "steady state" test and may require periodic administration over an extended time period ranging from several days to a week or more. Of course, since a patient reaches steady state in such a test, continuing the test for a longer time period should not affect the results. Further, when testing blood plasma levels in such a test, if the time period for testing exceeds the interval between doses, it is important the regimen be stopped after the test is begun so that observations of change in blood level and pain relief may be made without a further dose affecting these parameters.

Study 5—Controlled Release 40 mg vs Immediate Release 4×10 mg under Fed and Fasting Conditions The objectives of this study were to assess the relative bioavailability of oxymorphone from oxymorphone controlled release (40 mg) compared to oxymorphone immediate release (4×10 mg) under both fasted and fed conditions, and to determine the effect of food on the bioavailability of oxymorphone from the controlled release formulation, oxymorphone CR, and from the immediate release formulation, oxymorphone IR.

This study had a single-center, open-label, analytically blinded, randomized, four-way crossover design. Subjects randomized to Treatment 5A and Treatment 5C, as described below, were in a fasted state following a 10-hour overnight fast. Subjects randomized to Treatment 5B and Treatment 5D, as described below, were in the fed state, having had a high fat meal, completed ten minutes prior to dosing. There was a 14-day washout interval between the four dose administrations. The subjects were confined to the clinic during each study period. Subject assigned to receive Treatment 5A and Treatment 5B were discharged from the clinic on Day 3 following the 48-hour procedures, and subjects assigned to receive Treatment 5C and Treatment 5D were discharged from the clinic on Day 2 following the 36-hour procedures. On Day 1 of each study period the subjects received one of four treatments:

Treatments 5A and 5B: Oxymorphone controlled release 40 mg tablets from Table 2. Subjects randomized to Treatment 5A received a single oral dose of one 40 mg oxymorphone controlled release tablet taken with 240 ml of water after a 10-hour fasting period. Subjects randomized to Treatment 5B received a single oral dose of one 40 mg oxymorphone controlled release tablet taken with 240 ml of water 10 minutes after a standardized high fat meal.

Treatments 5C and 5D: Immediate release tablet (IR) 4×10 mg Oxymorphone. Subjects randomized to Treatment 5C received a single oral dose of 4×10 mg oxymorphone IR tablet taken with 240 ml of water after a 10-hour fasting period. Subjects randomized to Treatment 5D received a single oral dose of 4×10 mg oxymorphone IR tablet taken with 240 ml of water 10 minutes after a standardized high-fat meal.

A total of 28 male subjects were enrolled in the study, and 25 subjects completed the study. A total of 28 subjects received at least one treatment. Only subjects who completed all 4 treatments were included in the summary statistics and statistical analysis.

Blood samples (7 ml) were collected during each study period at the 0 hour (predose), and at 0.25, 0.5, 0.75, 1.0, 1.5, 2, 3, 4, 5, 6, 8, 10, 12, 24, 36, 48, 60, and 72 hours post-dose (19 samples) for subjects randomized to all Treatments.

The data for mean oxymorphone plasma concentration versus time for Treatments 5A, 5B, 5C, and 5D is contained in Table 22. The arithmetic means of the plasma oxymorphone pharmacokinetic parameters and the statistics for all Treatments are summarized in Table 23.

TABLE 22

Mean Plasma Concentration vs. Time (ng/ml)

| Time (hr) | Treatment 5A | Treatment 5B | Treatment 5C | Treatment 5D |
|---|---|---|---|---|
| 0 | 0.00 | 0.00 | 0.00 | 0.00 |
| 0.25 | 0.47 | 0.22 | 3.34 | 1.79 |
| 0.50 | 1.68 | 0.97 | 7.28 | 6.59 |
| 0.75 | 1.92 | 1.90 | 6.60 | 9.49 |
| 1 | 2.09 | 2.61 | 6.03 | 9.91 |
| 1.5 | 2.18 | 3.48 | 4.67 | 8.76 |
| 2 | 2.18 | 3.65 | 3.68 | 7.29 |
| 3 | 2.00 | 2.86 | 2.34 | 4.93 |
| 4 | 1.78 | 2.45 | 1.65 | 3.11 |
| 5 | 1.86 | 2.37 | 1.48 | 2.19 |
| 6 | 1.67 | 2.02 | 1.28 | 1.71 |
| 8 | 1.25 | 1.46 | 0.92 | 1.28 |
| 10 | 1.11 | 1.17 | 0.78 | 1.09 |
| 12 | 1.34 | 1.21 | 1.04 | 1.24 |
| 24 | 0.55 | 0.47 | 0.40 | 0.44 |
| 36 | 0.21 | 0.20 | 0.16 | 0.18 |
| 48 | 0.06 | 0.05 | 0.04 | 0.05 |
| 60 | 0.03 | 0.01 | 0.01 | 0.01 |
| 72 | 0.00 | 0.00 | 0.00 | 0.00 |

TABLE 23

Pharmacokinetic Parameters of Plasma Oxymorphone for Study 5

| | Treatment 5A | | Treatment 5B | | Treatment 5C | | Treatment 5D | |
|---|---|---|---|---|---|---|---|---|
| | Mean | SD | Mean | SD | Mean | SD | Mean | SD |
| $C_{max}$ | 2.79 | 0.84 | 4.25 | 1.21 | 9.07 | 4.09 | 12.09 | 5.42 |
| $T_{max}$ | 2.26 | 2.52 | 1.96 | 1.06 | 0.69 | 0.43 | 1.19 | 0.62 |
| $AUC_{(0-t)}$ | 35.70 | 10.58 | 38.20 | 11.04 | 36.00 | 12.52 | 51.35 | 20.20 |
| $AUC_{(0-inf)}$ | 40.62 | 11.38 | 41.17 | 10.46 | 39.04 | 12.44 | 54.10 | 20.26 |
| $T_{1/2el}$ | 12.17 | 7.57 | 10.46 | 5.45 | 11.65 | 6.18 | 9.58 | 3.63 |

The relative bioavailability calculations are summarized in Tables 24 and 25.

TABLE 24

Relative Bioavailability Determination Based on $AUC_{(0-inf)}$

| $F_{rel}$ (5D vs. 5C) | $F_{rel}$ (5B vs. 5A) |
|---|---|
| 1.3775 | 1.0220 |

TABLE 25

| $F_{rel}$ (5D vs. 5C) | $F_{rel}$ (5B vs. 5A) |
|---|---|
| 1.4681 | 1.0989 |

The data for mean 6-OH oxymorphone plasma concentration versus time for Treatments 5A, 5B, 5C, and 5D is contained in Table 26.

TABLE 26

Mean Plasma Concentration vs. Time (ng/ml)
6-Hydroxyoxymorphone

| Time (hr) | Treatment 5A | Treatment 5B | Treatment 5C | Treatment 5D |
|---|---|---|---|---|
| 0 | 0.00 | 0.00 | 0.00 | 0.00 |
| 0.25 | 0.27 | 0.05 | 2.36 | 0.50 |
| 0.50 | 1.32 | 0.31 | 5.35 | 1.98 |
| 0.75 | 1.37 | 0.59 | 4.53 | 2.97 |
| 1 | 1.44 | 0.82 | 3.81 | 2.87 |
| 1.5 | 1.46 | 1.09 | 2.93 | 2.58 |
| 2 | 1.46 | 1.28 | 2.37 | 2.29 |
| 3 | 1.39 | 1.14 | 1.69 | 1.72 |
| 4 | 1.25 | 1.14 | 1.33 | 1.26 |
| 5 | 1.02 | 1.00 | 1.14 | 1.01 |
| 6 | 0.93 | 0.86 | 0.94 | 0.86 |
| 8 | 0.69 | 0.72 | 0.73 | 0.77 |
| 10 | 0.68 | 0.67 | 0.66 | 0.75 |
| 12 | 0.74 | 0.66 | 0.70 | 0.77 |
| 24 | 0.55 | 0.52 | 0.54 | 0.61 |
| 36 | 0.23 | 0.30 | 0.28 | 0.27 |
| 48 | 0.18 | 0.20 | 0.20 | 0.19 |
| 60 | 0.09 | 0.10 | 0.09 | 0.09 |
| 72 | 0.06 | 0.06 | 0.04 | 0.05 |

TABLE 27

Pharmacokinetic Parameters of Plasma
6-Hydroxyoxymorphone for Study 5

| | Treatment 5A | | Treatment 5B | | Treatment 5C | | Treatment 5D | |
|---|---|---|---|---|---|---|---|---|
| | Mean | SD | Mean | SD | Mean | SD | Mean | SD |
| $C_{max}$ | 1.88 | 0.69 | 1.59 | 0.63 | 6.41 | 3.61 | 3.79 | 1.49 |
| $T_{max}$ | 1.48 | 1.18 | 2.73 | 1.27 | 0.73 | 0.47 | 1.18 | 0.74 |
| $AUC_{(0-t)}$ | 28.22 | 10.81 | 26.95 | 11.39 | 33.75 | 10.29 | 32.63 | 13.32 |
| $AUC_{(0-inf)}$ | 33.15 | 11.25 | 32.98 | 10.68 | 37.63 | 17.01 | 36.54 | 13.79 |
| $T_{1/2el}$ | 17.08 | 7.45 | 21.92 | 8.41 | 16.01 | 6.68 | 16.21 | 7.42 |

The above description incorporates preferred embodiments and examples as a means of describing and enabling the invention to be practiced by one of skill in the art. It is imagined that changes can be made without departing from the spirit and scope of the invention described herein and defined in the appended claims.

What is claimed is:

1. An analgesically effective controlled release pharmaceutical composition for oral delivery, comprising about 5 mg to about 80 mg oxymorphone or a pharmaceutically acceptable salt of oxymorphone and a controlled release matrix with a release rate profile designed to provide an adequate blood plasma level of oxymorphone over at least 12 hours to provide sustained pain relief over this same period wherein:
   (a) oxymorphone is the sole active ingredient in the composition;
   (b) the controlled release matrix comprises a hydrophilic material which forms a gel upon exposure to gastrointestinal fluid, wherein the hydrophilic material comprises at least one of:
      i. a heteropolysaccharide; or
      ii. a heteropolysaccharide and a cross-linking agent capable of cross-linking the heteropolysaccharide; or
      iii. a mixture of (i), (ii) and a polysaccharide gum; and
   (c) upon oral administration of the composition to a subject in need of an analgesic effect the blood plasma level of oxymorphone displays two or three peaks over the first 12 hours after administration,
   wherein the blood plasma levels of 6-OH oxymorphone and oxymorphone exhibit a ratio of $AUC_{(0-inf)}$ of blood plasma level versus time for 6-OH oxymorphone compared to oxymorphone in a range of about 0.5 to about 1.5.

2. The composition of claim 1 wherein the hydrophilic material is a polysaccharide.

3. The composition of claim 1 wherein the hydrophilic material is selected from the group consisting of a gum, a cellulose ether, an acrylic resin, a protein-derived material, and mixtures thereof.

4. The composition of claim 1 wherein the hydrophilic material is a gum selected from the group consisting of a heteropolysaccharide gum, a homopolysaccharide gum, and mixtures thereof.

5. The composition of claim 4 wherein the gum is selected from the group consisting of xanthan, tragacanth, acacia, karaya, alginates, agar, guar, hydroxypropyl guar, carrageenan, locust bean, and mixtures thereof.

6. The composition of claim 1 wherein the hydrophilic material is a cellulose ether selected from the group consisting of a hydroxyalkyl cellulose, a carboxyalkyl cellulose, and mixtures thereof.

7. The composition of claim 1 wherein the hydrophilic material is selected from the group consisting of hydroxyethyl cellulose, hydroxypropyl cellulose, hydroxypropyl methylcellulose, carboxymethylcellulose, and mixtures thereof.

8. The composition of claim 1 wherein the heteropolysaccharide is a water soluble polysaccharide containing two or more kinds of sugar units and having a branched or helical configuration.

9. The composition of claim 1 wherein the heteropolysaccharide is selected from the group consisting of xanthan gum, deacylated xanthan gum, carboxymethyl ether xanthan gum, propylene glycol ester xanthan gum and mixtures thereof.

10. The composition of claim 1 wherein the cross-linking agent is a homopolysaccharide gum.

11. The composition of claim 10 wherein the homopolysaccharide gum is locust bean gum.

12. The composition of claim 1 further comprising a filler selected from the group consisting of sucrose, dextrose, lactose, microcrystalline cellulose, fructose, xylitol, sorbitol, and mixtures thereof.

13. The composition of claim 1 wherein upon oral administration of a single dose thereof the oxymorphone $C_{max}$ is at least about 50% higher when the dosage form is administered to the subject under fed as compared to fasted conditions.

14. The composition of claim 1 wherein the composition comprises about 40 mg oxymorphone, and wherein the oxymorphone $C_{max}$ is about 58% higher when the composition is administered to the subject under fed as compared to fasted conditions.

15. The composition of claim 1 wherein the heteropolysaccharide and the agent capable of cross-linking the heteropolysaccharide are present in a weight ratio of about 1:3 to about 3:1.

16. The composition of claim 1 wherein the heteropolysaccharide and the agent capable of cross-linking the heteropolysaccharide are present in a weight ratio of about 1:1.

17. The composition of claim 1 wherein the controlled release matrix further comprises a hydrophobic polymer.

18. The composition of claim 17 wherein the hydrophobic polymer is selected from hydrophobic cellulosic materials, polymers or copolymers derived from acrylic or methacrylic acid esters, copolymers of acrylic and methacrylic acid esters, zein, waxes, shellac, and hydrogenated vegetable oils.

19. The composition of claim 17 wherein the hydrophobic polymer comprises an alkyl cellulose.

20. The composition of claim 1 further comprising a cationic cross-linking agent.

21. The composition of claim 20 wherein the cationic cross-linking agent is an alkali metal sulfate, chloride, borate, bromide, citrate, acetate or lactate or an alkaline earth metal sulfate, chloride, borate, bromide, citrate, acetate or lactate.

22. The composition of claim 20 wherein the cationic cross-linking agent is selected from calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate and sodium fluoride.

23. The composition of claim 20 wherein the cationic cross-linking agent is present in an amount of about 0.5% to about 16%, by weight of the composition.

24. The composition of claim 1 wherein the weight ratio of heteropolysaccharide to oxymorphone is in the range of about 10:1 to about 1:10.

25. The composition of claim 1 wherein the oxymorphone is present in an amount of about 20 mg.

26. The composition of claim 1 wherein the controlled release delivery system comprises about 10% to about 99% of a gelling agent comprising a heteropolysaccharide gum and a homopolysaccharide gum, about 1% to about 20% of a cationic crosslinking agent, and about 0% to about 89% of an inert diluent, by total weight of the controlled release delivery system.

27. The composition of claim 1 wherein the controlled release delivery system comprises about 10% to about 75% of a gelling agent, about 2% to about 15% of a cationic crosslinking agent, and about 30% to about 75% of an inert diluent, by total weight of the controlled release delivery system.

28. The composition of claim 1 wherein the controlled release delivery system comprises about 30% to about 75% of a gelling agent, about 5% to about 10% of a cationic cross linking agent, about 15% to about 65% of an inert diluent, by total weight of the controlled release delivery system.

29. An analgesically effective controlled release pharmaceutical composition for oral delivery, comprising about 5 mg to about 80 mg of oxymorphone or a pharmaceutically acceptable salt of oxymorphone and a controlled release matrix with a release rate profile designed to provide an adequate blood plasma level of oxymorphone over at least 12 hours to provide sustained pain relief over this same period wherein oxymorphone is the sole active ingredient in the composition, and wherein the blood plasma levels of 6-OH oxymorphone and oxymorphone exhibit a ratio of $AUC_{(0-inf)}$ of blood plasma level versus time for 6-OH oxymorphone compared to oxymorphone in a range of about 0.5 to about 1.5.

30. The composition of claim 29 wherein the controlled release matrix comprises a hydrophilic material.

31. The composition of claim 30 wherein the hydrophilic material is a polysaccharide.

32. The composition of claim 30 wherein the hydrophilic material is selected from the group consisting of a gum, a cellulose ether, an acrylic resin, a protein-derived material, and mixtures thereof.

33. The composition of claim 30 wherein the hydrophilic material is a gum selected from the group consisting of a heteropolysaccharide gum, a homopolysaccharide gum, and mixtures thereof.

34. The composition of claim 33 wherein the gum is selected from the group consisting of xanthan, tragacanth, acacia, karaya, alginates, agar, guar, hydroxypropyl guar, carrageenan, locust bean, and mixtures thereof.

35. The composition of claim 30 wherein the hydrophilic material is a cellulose ether selected from the group consisting of a hydroxyalkyl cellulose, a carboxyalkyl cellulose, and mixtures thereof.

36. The composition of claim 30 wherein the hydrophilic material is selected from the group consisting of hydroxyethyl cellulose, hydroxypropyl cellulose, hydroxypropyl methylcellulose, carboxymethylcellulose, and mixtures thereof.

37. The composition of claim 30 wherein the hydrophilic material comprises a heteropolysaccharide.

38. The composition of claim 37 further comprising a cross-linking agent capable of cross-linking the heteropolysaccharide.

39. The composition of claim 37 wherein the heteropolysaccharide is a water soluble polysaccharide containing two or more kinds of sugar units and having a branched or helical configuration.

40. The composition of claim 37 wherein the heteropolysaccharide is selected from the group consisting of xanthan gum, deacylated xanthan gum, carboxymethyl ether xanthan gum, propylene glycol ester xanthan gum and mixtures thereof.

41. The composition of claim 38 wherein the cross-linking agent comprises a homopolysaccharide gum.

42. The composition of claim 38 wherein the cross-linking agent is a homopolysaccharide gum.

43. The composition of claim 41 wherein the homopolysaccharide gum is locust bean gum.

44. The composition of claim 30 further comprising a filler selected from the group consisting of sucrose, dextrose, lactose, microcrystalline cellulose, fructose, xylitol, sorbitol, and mixtures thereof.

45. The composition of claim 29 wherein upon oral administration thereof the oxymorphone $C_{max}$ is at least about 50% higher when the dosage form is administered to the subject under fed as compared to fasted conditions.

46. The composition of claim 29 wherein the composition comprises about 40 mg oxymorphone, and wherein the oxymorphone $C_{max}$ is about 58% higher when the composition is administered to the subject under fed as compared to fasted conditions.

47. The composition of claim 38 wherein the heteropolysaccharide and the agent capable of cross-linking the heteropolysaccharide are present in a weight ratio of about 1:3 to about 3:1.

48. The composition of claim 38 wherein the heteropolysaccharide and the agent capable of cross-linking the heteropolysaccharide are present in a weight ratio of about 1:1.

49. The composition of claim 30 wherein the controlled release matrix further comprises a hydrophobic polymer.

50. The composition of claim 49 wherein the hydrophobic polymer is selected from hydrophobic cellulosic materials, polymers or copolymers derived from acrylic or methacrylic acid esters, copolymers of acrylic and methacrylic acid esters, zein, waxes, shellac, and hydrogenated vegetable oils.

51. The composition of claim 49 wherein the hydrophobic polymer comprises an alkyl cellulose.

52. The composition of claim 30 further comprising a cationic cross-linking agent.

53. The composition of claim 52 wherein the cationic cross-linking agent is an alkali metal sulfate, chloride, borate, bromide, citrate, acetate or lactate or an alkaline earth metal sulfate, chloride, borate, bromide, citrate, acetate or lactate.

54. The composition of claim 52 wherein the cationic cross-linking agent is selected from calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate and sodium fluoride.

55. The composition of claim 52 wherein the cationic cross-linking agent is present in an amount of about 0.5% to about 16%, by weight of the composition.

56. The composition of claim 37 wherein the weight ratio of heteropolysaccharide to oxymorphone is in the range of about 10:1 to about 1:10.

57. The composition of claim 29 wherein the oxymorphone is present in an amount of about 20 mg.

58. The composition of claim 29 wherein the controlled release delivery system comprises about 10% to about 99% of a gelling agent comprising a heteropolysaccharide gum and a homopolysaccharide gum, about 1% to about 20% of a cationic crosslinking agent, and about 0% to about 89% of an inert diluent, by total weight of the controlled release delivery system.

59. The composition of claim 29 wherein the controlled release delivery system comprises about 10% to about 75% of a gelling agent, about 2% to about 15% of a cationic crosslinking agent, and about 30% to about 75% of an inert diluent, by total weight of the controlled release delivery system.

60. The composition of claim 29 wherein the controlled release delivery system comprises about 30% to about 75% of a gelling agent, about 5% to about 10% of a cationic cross linking agent, about 15% to about 65% of an inert diluent, by total weight of the controlled release delivery system.

61. An analgesically effective controlled release pharmaceutical composition for oral delivery, comprising:
  a. a controlled release delivery matrix with a release rate profile designed to provide adequate blood plasma levels of oxymorphone and 6-hydroxy-oxymorphone over at least 12 hours to provide sustained pain relief over this same period, the matrix comprising a hydrophilic material, wherein the hydrophilic material comprises at least one of:
    i. a heteropolysaccharide; or
    ii. a heteropolysaccharide and a cross-linking agent capable of cross-linking the heteropolysaccharide; or
    iii. a mixture of (i), (ii) and a polysaccharide gum; and
  b. about 5 mg to about 80 mg of oxymorphone or a pharmaceutically acceptable salt of oxymorphone, wherein oxymorphone is the sole active ingredient, wherein upon placement of the composition in an in vitro release rate test, about 58% to about 80%, by weight, of the oxymorphone or salt thereof is released from the tablet at about 4 hours in the test.

62. The composition of claim 61, wherein upon oral administration of a single dose of the composition to a human subject, the oxymorphone Cmax is at least 50% higher when the dose is administered to the subject under fed as compared to fasted conditions.

63. The composition of claim 61, wherein upon placement of the composition in an in vitro release rate test, about 27% to about 33%, by weight, of the oxymorphone or salt thereof is released from the tablet at about 1 hour in the test, about 40% to about 48%, by weight, of the oxymorphone or salt thereof is released from the tablet at about 2 hours in the test, about 50% to about 59%, by weight, of the oxymorphone or salt thereof is released from the tablet at about 3 hours in the test, about 64% to about 74%, by weight, of the oxymorphone or salt thereof is released from the tablet at about 5 hours in the test, about 70% to about 84%, by weight, of the oxymorphone or salt thereof is released from the tablet at about 6 hours in the test, about 79% to about 92%, by weight, of the oxymorphone or salt thereof is released from the tablet at about 8 hours in the test, at least 85%, by weight, of the oxymorphone or salt thereof is released from the tablet at about 10 hours in the test, and at least 89%, by weight, of the oxymorphone or salt thereof is released from the tablet at about 12 hours in the test.

64. The composition of claim 61, wherein upon placement of the composition in an in vitro release rate test, about 27% to about 50%, by weight, of the oxymorphone or salt thereof is released from the tablet at about 1 hour in the test.

65. The composition of claim 61, wherein upon placement of the composition in an in vitro release rate test, about 40% to about 48%, by weight, of the oxymorphone or salt thereof is released from the tablet at about 2 hours in the test.

66. The composition of claim 61, wherein upon placement of the composition in an in vitro release rate test, about 50% to about 59%, by weight, of the oxymorphone or salt thereof is released from the tablet at about 3 hours in the test.

67. The composition of claim 61, wherein upon placement of the composition in an in vitro release rate test, about 64% to about 74%, by weight, of the oxymorphone or salt thereof is released from the tablet at about 5 hours in the test.

68. The composition of claim 61, wherein upon placement of the composition in an in vitro release rate test, about 70% to about 84%, by weight, of the oxymorphone or salt thereof is released from the tablet at about 6 hours in the test.

69. The composition of claim 61, wherein upon placement of the composition in an in vitro release rate test, about 79% to about 92%, by weight, of the oxymorphone or salt thereof is released from the tablet at about 8 hours in the test.

70. The composition of claim 61, wherein upon placement of the composition in an in vitro release rate test, at least 85%, by weight, of the oxymorphone or salt thereof is released from the tablet at about 10 hours in the test.

71. The composition of claim 61, wherein upon placement of the composition in an in vitro release rate test, at least 89%, by weight, of the oxymorphone or salt thereof is released from the tablet at about 12 hours in the test.

* * * * *